United States Patent
Carlson et al.

(10) Patent No.: US 8,165,683 B2
(45) Date of Patent: Apr. 24, 2012

(54) METHOD AND APPARATUS FOR DETECTION OF NERVOUS SYSTEM DISORDERS

(75) Inventors: David L. Carlson, Fridley, MN (US); Eric J. Panken, Edina, MN (US); Touby A. Drew, Minneapolis, MN (US); Jonathan C. Werder, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 225 days.

(21) Appl. No.: 11/609,465

(22) Filed: Dec. 12, 2006

(65) Prior Publication Data
US 2008/0046024 A1    Feb. 21, 2008

Related U.S. Application Data

(60) Provisional application No. 60/794,017, filed on Apr. 21, 2006.

(51) Int. Cl.
*A61N 1/36* (2006.01)
(52) U.S. Cl. ............... 607/45; 600/544; 600/545
(58) Field of Classification Search ............... 600/544, 600/545; 607/45
See application file for complete search history.

(56) References Cited

U.S. PATENT DOCUMENTS

| | | | |
|---|---|---|---|
| 3,498,287 A | 3/1970 | Ertl | |
| 3,841,309 A | 10/1974 | Salter | |
| 4,060,716 A | 11/1977 | Pekrul et al. | |
| 4,663,703 A | 5/1987 | Axelby et al. | |
| 4,791,548 A | 12/1988 | Yoshikawa et al. | |
| 4,868,773 A | 9/1989 | Coyle et al. | |
| 4,974,602 A | 12/1990 | Abraham-Fuchs | |
| 4,998,051 A | 3/1991 | Ito | |
| 5,311,876 A | 5/1994 | Olsen et al. | |
| 5,331,969 A | 7/1994 | Silberstein | |
| 5,345,535 A | 9/1994 | Doddington | |
| 5,347,446 A | 9/1994 | Iino et al. | |
| 5,349,962 A | 9/1994 | Lockard | |
| 5,488,560 A | 1/1996 | Wood et al. | |
| 5,519,605 A | 5/1996 | Cawlfield | |
| 5,583,963 A | 12/1996 | Lozach | |
| 5,694,342 A | 12/1997 | Stein | |
| 5,707,334 A | 1/1998 | Young | |
| 5,818,929 A | 10/1998 | Yaguchi | |

(Continued)

FOREIGN PATENT DOCUMENTS
EP    0433626    6/1991
(Continued)

OTHER PUBLICATIONS

International Search and the Written Opinion, dated Mar. 10, 2008 for PCT Application No. PCT/US2007/066334 (11 pages).

(Continued)

*Primary Examiner* — Carl H Layno
*Assistant Examiner* — Jennifer Stewart

(57) ABSTRACT

Systems and methods for detecting and/or treating nervous system disorders, such as seizures. Certain embodiments of the invention relate generally to implantable medical devices (IMDs) adapted to detect and treat nervous system disorders in patients with an IMD. Certain embodiments of the invention include detection of seizures based upon comparisons of long-term and short-term representations of physiological signals. Other embodiments include prediction of seizure activity based upon analysis of physiological signal levels. An embodiment of the invention monitors the quality of physiological signals, and may be able to compensate for signals of low signal quality. A further embodiment of the invention includes detection of seizure activity following the delivery of therapy.

32 Claims, 21 Drawing Sheets

U.S. PATENT DOCUMENTS

| | | | |
|---|---|---|---|
| 5,857,978 | A | 1/1999 | Hively |
| 5,928,272 | A | 7/1999 | Adkins et al. |
| 5,995,868 | A | 11/1999 | Dorfmeister et al. |
| 6,066,163 | A | 5/2000 | John |
| 6,081,144 | A | 6/2000 | Usuki et al. |
| 6,098,463 | A | 8/2000 | Goldberg |
| 6,121,817 | A | 9/2000 | Yang et al. |
| 6,167,298 | A | 12/2000 | Levin |
| 6,341,236 | B1 | 1/2002 | Osorio et al. |
| 6,442,421 | B1 | 8/2002 | Le Van Quyen |
| 6,442,506 | B1 | 8/2002 | Trevino |
| 6,463,328 | B1 | 10/2002 | John |
| 6,473,639 | B1 | 10/2002 | Fischell et al. |
| 6,473,732 | B1 | 10/2002 | Chen |
| 6,480,743 | B1 | 11/2002 | Kirkpatrick |
| 6,549,804 | B1 | 4/2003 | Osorio |
| 6,587,727 | B2 | 7/2003 | Osorio et al. |
| 6,658,287 | B1 | 12/2003 | Litt et al. |
| 6,768,969 | B1 | 7/2004 | Nikitin et al. |
| 6,904,390 | B2 | 6/2005 | Nikitin et al. |
| 6,920,357 | B2 | 7/2005 | Osorio et al. |
| 7,146,211 | B2 | 12/2006 | Frei et al. |
| 7,761,145 | B2 | 7/2010 | Virag et al. |
| 7,761,146 | B2 | 7/2010 | Carlson |
| 7,764,989 | B2 | 7/2010 | Carlson |
| 2001/0051819 | A1 | 12/2001 | Fischell et al. |
| 2002/0077557 | A1 | 6/2002 | Cheng |
| 2002/0103512 | A1 | 8/2002 | Echauz et al. |
| 2003/0004428 | A1 | 1/2003 | Pless et al. |
| 2003/0149456 | A1 | 8/2003 | Rottenberg et al. |
| 2003/0187621 | A1 | 10/2003 | Nikitin et al. |
| 2003/0195574 | A1 | 10/2003 | Osorio et al. |
| 2004/0006264 | A1 | 1/2004 | Mojarradi et al. |
| 2004/0133119 | A1 | 7/2004 | Osorio et al. |
| 2004/0133120 | A1 | 7/2004 | Frei et al. |
| 2004/0133248 | A1 | 7/2004 | Frei et al. |
| 2004/0133390 | A1 | 7/2004 | Osorio et al. |
| 2004/0136453 | A1 | 7/2004 | Lin et al. |
| 2004/0138516 | A1 | 7/2004 | Osorio et al. |
| 2004/0138517 | A1 | 7/2004 | Osorio et al. |
| 2004/0138518 | A1 | 7/2004 | Rise et al. |
| 2004/0138536 | A1 | 7/2004 | Frei et al. |
| 2004/0138581 | A1 | 7/2004 | Frei et al. |
| 2004/0138647 | A1 | 7/2004 | Osorio et al. |
| 2004/0138711 | A1 | 7/2004 | Osorio et al. |
| 2004/0152958 | A1 | 8/2004 | Frei et al. |
| 2004/0158119 | A1 | 8/2004 | Osorio et al. |
| 2004/0181263 | A1 | 9/2004 | Balzer et al. |
| 2004/0230105 | A1 | 11/2004 | Geva |
| 2005/0010265 | A1 | 1/2005 | Baru Fassio et al. |
| 2005/0021313 | A1 | 1/2005 | Nikitin et al. |
| 2005/0182338 | A1 | 8/2005 | Huiku |
| 2005/0197590 | A1 | 9/2005 | Osorio et al. |
| 2005/0261601 | A1* | 11/2005 | Schuler et al. ............ 600/545 |
| 2006/0015153 | A1 | 1/2006 | Gliner |
| 2006/0058851 | A1 | 3/2006 | Cigaina |
| 2006/0069322 | A1 | 3/2006 | Zhang et al. |
| 2006/0079936 | A1 | 4/2006 | Boveja |
| 2006/0094972 | A1 | 5/2006 | Drew |
| 2006/0094973 | A1 | 5/2006 | Drew |
| 2008/0046024 | A1 | 2/2008 | Carlson |
| 2008/0228100 | A1 | 9/2008 | Navakatikyan |
| 2010/0042180 | A1 | 2/2010 | Mueller |

FOREIGN PATENT DOCUMENTS

| | | |
|---|---|---|
| EP | 1500409 | 1/2005 |
| WO | WO9309841 | 5/1993 |
| WO | 9515117 | 6/1995 |
| WO | 9726823 | 7/1997 |
| WO | 0175660 | 10/2001 |
| WO | WO0236003 | 5/2002 |
| WO | 02089913 | 11/2002 |
| WO | 2004034883 | 4/2004 |
| WO | 2004034982 | 4/2004 |
| WO | 2004043536 | 5/2004 |
| WO | WO2004064918 | 8/2004 |
| WO | 2005061045 | 7/2005 |

OTHER PUBLICATIONS

International Search and the Written Opinion, dated Mar. 10, 2008 for PCT Application No. PCT/US2007/061152 (12 pages).

International Search and the Written Opinion, dated Mar. 10, 2008 for PCT Application No. PCT/US2007/061141 (12 pages).

International Search and the Written Opinion, dated Jul. 24, 2007 for PCT Application No. PCT/US2007/061138 (9 pages).

International Search and the Written Opinion, dated May 25, 2007 for PCT Application No. PCT/US2007/061150 (14 pages).

International Search and the Written Opinion, dated May 18, 2007 for PCT Application No. PCT/US2007/061143 (11 pages).

International Search and the Written Opinion, dated Jul. 3, 2007 for PCT Application No. PCT/US2007/061147 (9 pages).

International Search and the Written Opinion, dated Jan. 21, 2008 for PCT Application No. PCT/US2007/061145 (9 pages).

International Preliminary Report on Patentability, dated Jun. 8, 2008 for PCT Application No. PCT/US2007/061141, 13 pages.

Sorting Continuous-Time Signals and the Analog Median Filter, Paulo J. S. G. Ferreira, IEEE Signal Processing Letters, vol. 7, No. 10, Oct. 2000, pp. 281-283.

A Review of Median Filter Systems for Analog Signal Processing, Tiina Jarske and Olli Vainio, Analog Integrated Circuits and Signal Processing 3, pp. 127-135.

Median Filtering by Threshold Decomposition, J. Patrick Fitch, Edward J. Coyle, and Neal C. Gallagher, Jr., IEEE Transactions on Acoustics, Speech, and Signal Processing, vol. ASSP-32, No. 6, Dec. 1984, pp. 1183-1188.

Design and Implementation of a Single-Chip 1-D Median Filter, Kemal Oflazer, IEEE Transactions on Acoustics, Spech and Signal Processing, vol. ASSP-31, No. 5, Oct. 1983, pp. 1164-1168.

Direct Analog Rank Filtering, Kiichi Urahama and Takeshi Nagao, IEEE Transactions on Circuits and Systems-I: Fundamental Theory and Applications, vol. 42, No. 7, Jul. 1995, pp. 385-388.

Harrison MAF, Osorio I, Lai YC, Frei MG. Correlation dimension and correlation integral are sensitive to ECoG amplitude and power spectral density variation. Abstract; Epilepsia. 42(S7);37. Proceeding of the American Epilepsy Society, American Clinical Neurophysiology Society Annual Meeting, Philadelphia, PA, Nov. 30-Dec. 5, 2001.

Design of a Switched-Current Median Filter, C. K. Tse and K. C. Chun, IEEE Transactions on Circuits and Systems-II: Analog and Digital Signal Processing, vol. 42, No. 5, May 1995, pp. 356-359.

OSNet: A Neural Network Implementation of Order Statistic Filters, Pingnan Shi and Rabab K. Ward, IEEE Transactions on Neural Networks, vol. 4, No. 2, Mar. 1993, pp. 234-241.

Abstract of Analog Implementation of Seizure Detection Algorithm, Nikitin et. al., BMES/EMBS Conference, 1999. Proceedings of the First Joint, Oct. 13-16, 1999, pp. 860 vol. 2.

Analog Implementation of Seizure Detection Algorithm, Nikitin et. al., Flint Hills Scientific LLC.

High Speed FPGA Implementation of Median Filters, Bela Feher and Gabor Szedo, NDES '98 Nonlinear Dynamics of Electronic Systems, Tech. University of Budapest, Hungary Jul. 16-18, 1998, pp. 191-219.

Deterministic Properties of Analog Median Filters, Murk J. Bottema, IEEE Transactions on Information Theory, vol. 37, No. 6, Nov. 1991, pp. 1629-1640.

Analysis of the Properties of Median and Weighted Median Filters Using Threshold Logic and Stack Filter Representation, Olli Yli-Harja, Jaakko Astola and Yrjo Neuvo, IEEE Transactions on Signal Processing, vol. 39, No. 2, Feb. 1991, pp. 395-410.

Properties of Analog Median Filters, Steffan Paul, Knut Huper adn Josef A. Nossek, Non-Linear Digital Signal Processing 1993, IEEE Writer Workshop Jan. 17-20, 1993.

Stack Filters, Peter D. Wendt, Edward J. Coyle, adn Neal C. Gallagher, IEEE Transactions on Acoustics, Speech and Signal Processing, vol. ASSP-34, No. 4, Aug. 1986, pp. 898-911.

Output Distributions of Recursive Stack Filters, Ilya Shmulevich, Olli Yli-Harja, Karen Egiazarian, and Jaakko Astola, IEEE Signal Processing Letters, vol. 6, No. 7, Jul. 1999, pp. 175-178.

Binary Partition Algorithms and VLSI Architectures for Median and Rank Order Filtering, Charng Long Lee and Chein-Wei Jen, IEEE Transactions on Signal Processing, vol. 41, No. 9, Sep. 1993, pp. 2937-2942.

A New Algorithm for Order Statistic and Sorting, Barun K. Kar and Dhiraj K. Pradhan, IEEE Transactions on Signal Processing, vol. 41, No. 8, Aug. 1993, pp. 2688-2694.

Frei, Mark G., Parametric Identification in Continusous-Time Stochastic Systems Using Time and Space Weighted Least Squares, Dissertation, Dec. 7, 1993, submitted to the University of Kansas Department of Mathematics.

Nikitin, Alexei V., Pulse Pileup Effects in Counting Detectors, Dissertation, submitted to the University of Kansas Department of Physics and Astronomy, published Aug. 29, 1999.

Nikitin, Alexei V. et al., Many-fold Coincidence Pileup in Silicon Detectors: Solar X-Ray Response of Charged Particle Detector System for Space, Elsevier Science, Aug. 16, 1996.

Nikitin, Alexei V., et al., The effect of pulse pile-up on threshold crossing rates in a system with a known impulse response, Elsevier Science, Nov. 15, 1997.

Harrison MAF, Frei MG, Asuri S, Osorio, I, Lai Y-C. Correlation dimension and integral do not predict epileptic seizures. Chaos. Jul. 26, 2005;15, 033106. doi:10.1063/1.1935138.

Harrison MAF, Frei MG, Osorio I. Accumulated energy revisited. Clin Neurophysiol. Mar. 2005;116(3):527-31. doi:10.1016/j.clinph.2004.08.022.

Lai Y-C, Harrison MAF, Frei MG, Osorio I. Reply to Comment on Inability of Lyapunov exponents to predict epileptic seizures.Physical Review Letters. 2005;94;019802.

Osorio I, Frei MG, Sunderam S, Giftakis J, Bhavaraju NC, Schaffner SF, Wilkinson SB. Automated seizure abatement in humans using electrical stimulation. Ann Neur. Jan. 24, 2005;57(2):258-68.

Sunderam S, Frei MG, Osorio I. Predictability of the interseizure interval demonstrated by using a discrete sequence of automated detection times. Abstract; Epilepsia. 2004;45(S7):284.

Bhavaraju NC, Frei MG, Osorio I. Real-time automated seizure detection and quantitative analysis in analog: method and performance evaluation. Abstract; Epilepsia. 2004;45(S7):327.

Osorio I, Frei MG, Sunderam S, Giftakis J, Bhavaraju NC, Schaffner SF, Wilkinson SB. Automated seizure abatement in humans using electrical stimulation. Abstract; Epilepsia. 2004;45(S7):330.

Graves NM, Lozano AM, Wennberg RA, Osorio I, Wilkinson S, Baluch G, French JA, Kerrigan JF Shetter A, Fisher RA. Brain stimulation for epilepsy: Pilot patient results and implementation of a controlled clinical trial. Abstract; Epilepsia 2004;45(S7):148.

Lai Y-C, Harrison MAH, Frei MG, Osorio I. Controlled test for predictive power of Lyapunov exponents: Their inability to predict epileptic seizures. Chaos. Sep. 2004;14(3):630-42.

Meng L, Frei MG, Osorio I, Strang G, Nguyen TQ. Gaussian mixture models of EcoG signal features for improved detection of epileptic seizure. Medical Engineering and Physics. 2004;26(5):379-93.

Harrison MAF, Osorio I, Frei MG, Lai Y-C, Asuri S. Seizure prediction and detection with correlation integrals. Abstract; Epilepsia. 2003; 44(S9):229. Proceedings of the American Epilepsy Society Meeting, Boston, MA. Dec. 5-10, 2003.

Lai Y-C, Harrison MAF, Frei MG, Osorio I. Inability of Lyapunov exponents to predict epileptic seizures. Phys Rev Lett. Aug. 8, 2003;91(6):068102.

Hass SH, Frei MG, Osorio I, Pasik-Duncan B, Radel J. EEG ocular artifact removal through ARMAX model system identification using extended least squares. Comm Info Systems. Jun. 2003;3(1):19-40.

Sunderam S and Osorio I. Mesial temporal lobe seizures may activate thermoregulatory mechanisms in Humans: An infrared study of facial temperature. Epilepsy and Behavior. Aug. 2003;4(4):399-406.

Osorio I, Frei MG, Giftakis J, Peters T, Ingram J, Turnbull M, Herzog M, Rise M, Schaffner S, Wennberg R, Walczak T, Risinger M, Ajomone-Marsan C. Performance re-assessment of a real-time seizure detection algorithm on long ECoG series. Epilepsia. Dec. 2002;43(12):1522-35.

Bhavaraju NC, Nagaraddi V, Chetlapalli SR, and Osorio I. Electrical and thermal behavior of non-ferrous noble metal electrodes exposed to MRI fields. Magnetic Resonance Imaging. May 2002;20(4):351-57.

Lai Y-C, Osorio I, Harrison MAF, Frei, MG. Correlation-dimension and autocorrelation fluctuations in seizure dynamics. Physical Review E Stat Nonlin Soft Matter Phys. Mar. 2002;65(3 Pt 1):031921.

Peters TE, Bhavaraju NC, Frei MG, Osorio I. Network system for automated seizure detection and contingent delivery of therapy. J Clin Neurophysiol. Nov. 2001;18(6):545-9.

Sunderam S, Osorio I, Watkins III JF, Wilkinson SB, Frei MG, and Davis RE. Vagal and sciatic nerve stimulation have complex timedependent effects on chemically induced seizures: A controlled study. Brain Res. Nov. 2001;9;918 (1-2):60-6.

Osorio I, Frei MG, Manly BFJ, Sunderam S, Bhavaraju NC, and Wilkinson SB. An introduction to contingent (closed-loop) brain electrical stimulation for seizure blockage, to ultra-short term t and to multidimensional statistical analysis of therapeutic efficacy. J Clin Neurophysiol. Nov. 2001;18(6):533-44.

Johnson AM, Frei MG, Sunderam S, Asuri S, Osorio I. Application of the intrinsic timescale decomposition (ITD) algorithm to EEG seizure detection. Abstract; Epilepsia. 42(S7);37. Proceeding of the American Epilepsy Society, American Clinical Neurophysiology Society Annual Meeting, Philadelphia, PA, Nov. 30-Dec. 5, 2001.

Ingram JL, Osorio I, Wilinson SB. Anterior thalamic neclei evoked responses: A preliminary study. Abstract; Epilepsia. 42(S7);29. Proceeding of the American Epilepsy Society, American Clinical Neurophysiology Society Annual Meeting, Philadelphia, PA, Nov. 30-Dec. 5, 2001.

Peters T, Frei MG, Bhavaraju NC, Sunderam S, Osorio I. Network system for bedside automated seizure detection and stimulation. Abstract; Epilepsia. 42(S7);40. Proceeding of the American Epilepsy Society, American Clinical Neurophysiology Society Annual Meeting, Philadelphia, PA, Nov. 30-Dec. 5, 2001.

Osorio I, Frei MG, Wilkinson SB, Sunderam S, Bhavaraju NC, Graves N, Schaffner SF, Peters T, Johnson AM, DiTeres, CA, Ingram J, Nagaraddi V, Overman J, Kavalir MA, Turnbull M. Seizure blockage with automated "closed-loop" electrical stimulation: A pilot study. Abstract; Epilepsia. 42(S7);207. Proceeding of the American Epilepsy Society, American Clinical Neurophysiology Society Annual Meeting, Philadelphia, PA, Nov. 30-Dec. 5, 2001.

Frei MG, Osorio I, Giftakis JE, Herzog MH, Rise MT, Schaffne, SF, Johnson AM, DiTeresi CA, Peters T, Ingram J, Ajmone-Marsan C. Performance assessment of FHS seizure detection algorithm on Long ECoG Series. Abstract; Epilepsia. 42(57);37. Proceeding of the American Epilepsy Society, American Clinical Neurophysiology Society Annual Meeting, Philadelphia, PA, Nov. 30-Dec. 5, 2001.

Bhavaraju NC, Nagaraddi V, Osorio I. Electrical and thermal behavior of intracranial electrodes during magnetic resonance imaging: A quantitative study. Abstract; Epilepsia. 42(S7);62. Proceeding of the American Epilepsy Society, American Clinical Neurophysiology Society Annual Meeting, Philadelphia, PA, Nov. 30-Dec. 5, 2001.

Thompson MM, Dubin JE, Eckard D, Troster AI, Osorio I. The WADA test has nonselective effects in the brain: A power spectral stydy. Abstract; Epilepsia. 42(S7);243. Proceeding of the American Epilepsy Society, American Clinical Neurophysiology Society Annual Meeting, Philadelphia, PA, Nov. 30-Dec. 5, 2001.

U.S. Appl. No. 11/609,446 Non Final Office Action mailed Apr. 10, 2009, 8 pgs.

U.S. Appl. No. 11/609,432 Non Final Office Action mailed Jan. 16, 2009, 9 pgs.

U.S. Appl. No. 11/609,432 Final Office Action mailed Jul. 6, 2009, 10 pgs.

U.S. Appl. No. 11/677,360 Non Final Office Action mailed May 21, 2009, 9 pgs.

U.S. Appl. No. 11/677,360 Non Final Office Action mailed Mar. 12, 2010, 11 pgs.

U.S. Appl. No. 11/609,485 Notice of Allowance mailed Mar. 29, 2010, 7 pgs.

U.S. Appl. No. 11/609,432 Non Final Office Action mailed Nov. 4, 2009, 10 pgs.

U.S. Appl. No. 11/609,420 Non Final Office Action mailed Jun. 11, 2009, 11 pgs.

U.S. Appl. No. 11/609,420 Notice of Allowance mailed Nov. 18, 2009, 4 pgs.

U.S. Appl. No. 11/677,360 Final Office Action mailed Nov. 9, 2009, 10 pgs.
U.S. Appl. No. 11/609,485 Non Final Office Action mailed Nov. 5, 2009, 10 pgs.
U.S. Appl. No. 11/609,420 Notice of Allowance mailed Apr. 6, 2010, 4 pgs.
U.S. Appl. No. 11/609,432 Notice of Allowance mailed Jun. 1, 2010, 8 pgs.
U.S. Appl. No. 11/677,360 Final Office Action mailed Oct. 13, 2010, 10 pgs.
U.S. Appl. No. 11/677,360 Notice of Allowance mailed Mar. 2, 2011, 4 pgs.
U.S. Appl. No. 12/694,728 Final Office Action mailed Apr. 12, 2011, 7 pgs.
U.S. Appl. No. 11/609,540 Office Action mailed Jun. 9, 2011, 22 pgs.
U.S. Appl. No. 12/694,728 Notice of Allowance mailed Jul. 20, 2011, 4 pgs.
U.S. Appl. No. 11/609,540 Office Action mailed Mar. 2, 2012, 16 pgs.
U.S. Appl. No. 12/816,055 Office Action mailed Dec. 29, 2011, 7 pgs.

* cited by examiner

METHOD AND APPARATUS FOR DETECTION OF NERVOUS SYSTEM DISORDERS

CROSS REFERENCE TO RELATED APPLICATIONS

This application claims priority to U.S. Provisional Patent Application Ser. No. 60/794,017, filed on Apr. 21, 2006, the contents of which are incorporated by reference.

FIELD OF THE INVENTION

The present invention relates generally to implantable medical devices (IMDs), and more particularly relates to systems and methods for detecting and/or treating nervous system disorders, such as seizures, in a patient with an IMD.

BACKGROUND OF THE INVENTION

Nervous system disorders affect millions of people, causing a degradation of life, and in some cases, death. Nervous system disorders include disorders of the central nervous system, peripheral nervous system, and mental health and psychiatric disorders. Such disorders include, for example without limitation, epilepsy, Parkinson's disease, essential tremor, dystonia, and multiple sclerosis (MS). Additionally, nervous system disorders include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (e.g., narcolepsy), obesity, and anorexia.

As an example, epilepsy is a serious neurological disease prevalent across all ages. Epilepsy is a group of neurological conditions in which a person has or is predisposed to recurrent seizures. A seizure is a clinical manifestation resulting from excessive, hypersynchronous, abnormal electrical or neuronal activity in the brain. A seizure is a type of adverse neurological event that may be indicative of a nervous system disorder. This electrical excitability of the brain may be likened to an intermittent electrical overload that manifests with sudden, recurrent, and transient changes of mental function, sensations, perceptions, and/or involuntary body movement. Because the seizures are unpredictable, epilepsy affects a person's employability, psychosocial life, and ability to operate vehicles or power equipment. It is a disorder that occurs in all age groups, socioeconomic classes, cultures, and countries. In developed countries, the age-adjusted incidence of recurrent unprovoked seizures ranges from 24/100,000 to 53/100,000 person-years and may be even higher in developing countries. In developed countries, age-specific incidence is highest during the first few months of life and again after age 70. The age-adjusted prevalence of epilepsy is 5 to 8 per 1,000 (0.5% to 0.8%) in countries where statistics are available. In the United States alone, epilepsy and seizures affect 2.3 million Americans, with approximately 181,000 new cases occurring each year. It is estimated that 10% of Americans will experience a seizure in their lifetimes, and 3% will develop epilepsy by age 75.

There are various approaches in treating nervous system disorders. Treatment therapies can include any number of possible modalities alone or in combination including, for example, electrical stimulation, magnetic stimulation, and/or drug infusion. Each of these treatment modalities can be operated using closed-loop feedback control. Such closed-loop feedback control techniques receive neurological signals (e.g., from a monitoring element) carrying information about a symptom or a condition or a nervous system disorder. Such a neurological signal can include, for example, electrical signals (such as electroencephalogram (EEG), electrocorticogram (ECoG), and/or electrocardiogram (EKG) signals), chemical signals, other biological signals (such as changes in the quantity of neurotransmitters), temperature signals, pressure signals (such as blood pressure, intracranial pressure or cardiac pressure), respiration signals, heart rate signals, pH-level signals, and peripheral nerve signals (such as cuff electrodes placed on a peripheral nerve). Monitoring elements can include, for example, recording electrodes or various types of sensors.

For example, U.S. Pat. No. 5,995,868 to Dorfmeister et al., incorporated herein by reference in relevant part, discloses a system for the prediction, rapid detection, warning, prevention, or control of changes in activity states in the brain of a patient. Use of such a closed-loop feed back system for treatment of a nervous system disorder may provide significant advantages. For example, it may be possible for treatment to be delivered before the onset of the symptoms of the nervous system disorder.

In the management of a nervous system disorder, it may be important to determine an extent of a neurological event, a location of the neurological event, a severity of the neurological event, and the occurrence of multiple neurological events in order to prescribe and/or provide a delivery of a treatment or otherwise manage the neurological disorder. A patient, for example, would not benefit from a medical device system if the patient experienced a neurological event but was not administered treatment because the medical device system did not detect the neurological event. On the other hand, a patient may suffer adverse effects, for example, if subjected to a degree of treatment corresponding to multiple neurological events, such as seizures, when in fact the patient had experienced only one neurological event, or a series of minor events, or no neurological event at all. As used herein, the term "neurological event" may encompass physiological events, such as seizures, as well as events defined artificially, for example, by measurable signal processing parameters.

GLOSSARY OF TERMS

The "onset of the clinical component" of a seizure is the earlier of either (1) the time at which a patient becomes is aware that a seizure is beginning (the "aura"), or (2) the time at which an observer recognizes a significant physical or behavioral change typical of a seizure.

The "onset of the electrographic component" of a seizure is defined by the appearance of a class of signal changes recognized as characteristic of a seizure. This analysis may typically include visual review of signal tracings of varying duration, both before and after the perceived signal changes, using multiple channels of information and clinical correlates. The precise determination of the onset is subject to personal interpretation, and may vary based on the skill and attention level of the reviewer, the quality of data, and its display.

An electroencephalogram, or EEG, usually refers to voltage potentials recorded from the scalp. The term "EEG" typically encompasses recordings made outside the dura mater. The electrocorticogram, or ECoG, typically refers to voltage potentials recorded intracranially, e.g., directly from the cortex. It should be noted that the methods and devices described herein may be applied to any signal representing electrical activity sensed from a patient's brain, including EEG and ECoG signals. For simplicity, the term "EEG" has been used throughout this disclosure, and is intended to encompass EEG and ECoG types of signals, as well as any other signals representing electrical activity sensed from a patient's brain.

The period of time during which a seizure is occurring is called the ictal period. Those skilled in the art will appreciate that the term ictal can be applied to phenomena other than seizures. Periods of time when a patient is not in a state of seizure, or in transition into or out of the seizure state, are known as interictal periods.

The term "false positive" refers to the case of a system mistakenly detecting a non-seizure signal and classifying it as a seizure. The term "false negative" describes the case in which a true seizure goes undetected by a system. Systems that have a low rate of false positive detections are called specific, while those with a low rate of false negative detections are called sensitive.

The term "epileptiform discharge" is used herein to refer to a class of sharply contoured waveforms, usually of relatively high signal energy, having a relatively brief duration (e.g., rarely exceeding about 200 msec). These epileptiform discharge signals (or "spikes") can form complexes with slow waves, and can occur in singlets or in multiplets.

BRIEF SUMMARY OF THE INVENTION

In certain embodiments of the invention, a method of detecting a neurological event includes acquiring an EEG signal comprising a stream of sampled data values, transforming the stream of sampled data values into a stream of data magnitude values, determining a long term representation of the EEG signal from the data magnitude values and deriving a magnitude threshold therefrom, comparing the data magnitude values to the magnitude threshold to produce a stream of comparator output values that indicate whether a given data magnitude value exceeds the magnitude threshold, and calculating an event monitoring parameter based on the comparator output values. A neurological event may be detected when the event monitoring parameter exceeds a threshold, for example.

In an exemplary embodiment, a computer readable medium may be programmed with instructions for performing a method of detecting a neurological event, the instructions adapted to cause a programmable processor to acquire a stream of sampled EEG signal data values, transforming the stream of sampled data values into a stream of data magnitude values, determining a long term representation of the EEG signal from the data magnitude values and deriving a magnitude threshold therefrom, comparing the data magnitude values to the magnitude threshold to produce a stream of comparator output values that indicate whether a given data magnitude value exceeds the magnitude threshold, and calculating an event monitoring parameter based on the comparator output values. A neurological event may be detected when the event monitoring parameter exceeds a threshold, for example.

In still another exemplary embodiment, an implantable medical device system for detecting a neurological event includes an implantable medical device (IMD) and at least one electrode adapted to communicate EEG signals to the IMD, the device being capable of acquiring an EEG signal comprising a stream of sampled data values, transforming the stream of sampled data values into a stream of data magnitude values, determining a long term representation of the EEG signal from the data magnitude values and deriving a magnitude threshold therefrom, comparing the data magnitude values to the magnitude threshold to produce a stream of comparator output values that indicate whether a given data magnitude value exceeds the magnitude threshold, and calculating an event monitoring parameter based on the comparator output values. A neurological event may be detected when the event monitoring parameter exceeds a threshold, for example. Further embodiments may be adapted to deliver therapy to a patient when a neurological event is detected.

BRIEF DESCRIPTION OF THE DRAWINGS

The present invention will hereinafter be described in conjunction with the following drawing figures, wherein like numerals denote like elements:

FIG. 13 also includes a series of time plots showing logical output states associated with a method of detecting a precursor to a neurological event according to an embodiment of the invention;

DETAILED DESCRIPTION OF THE INVENTION

Figure 1:
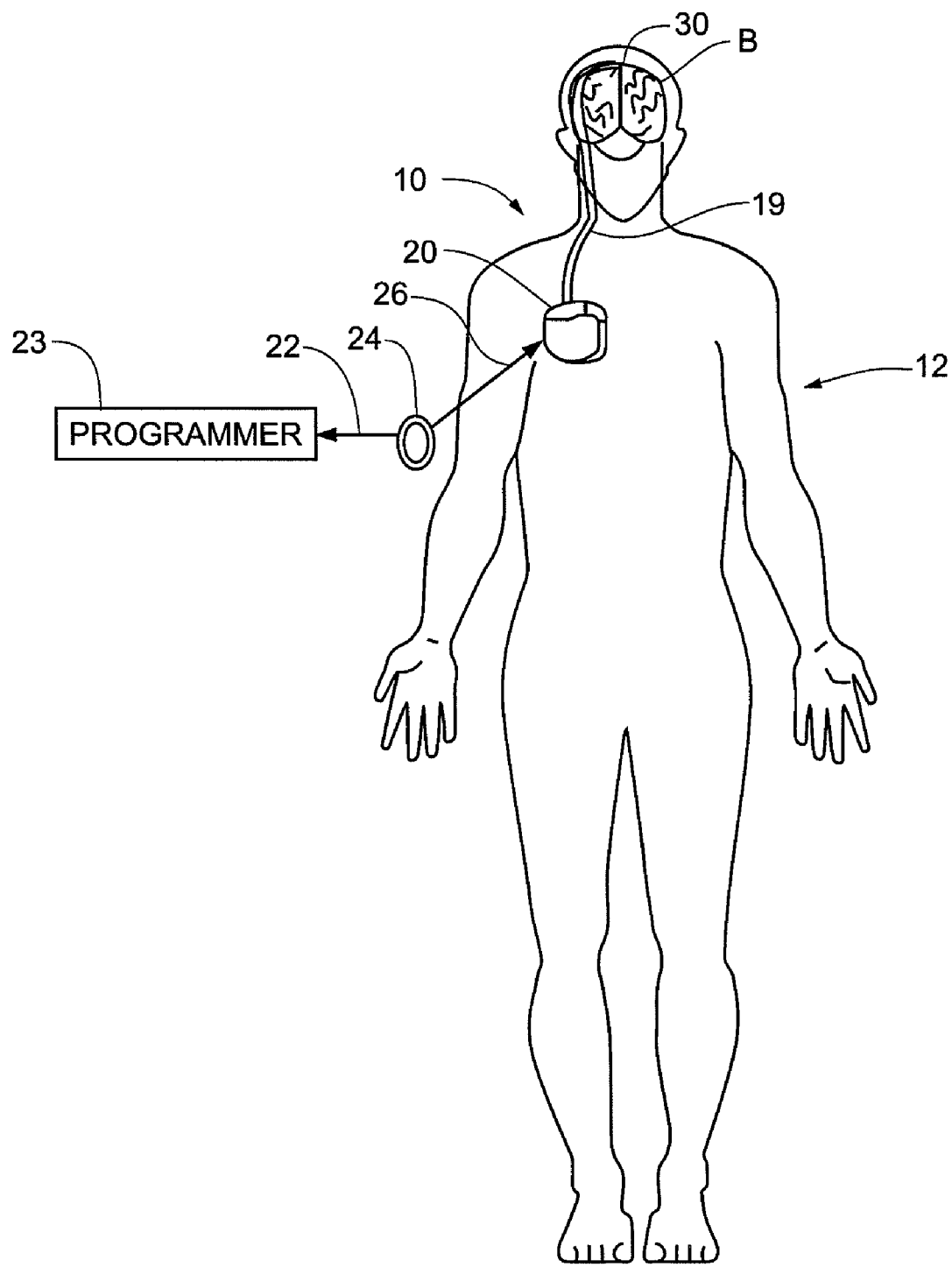
FIG. 1 shows an implantable system for treating a nervous system disorder according to an embodiment of the invention.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention as claimed.

FIG. 1 shows an embodiment of an implanted system 10 for treatment of a nervous system disorder in accordance with an embodiment of the invention. System 10 includes IMD 20, lead(s) 19, and electrode(s) 30. Although the implanted system 10 is discussed herein in the context of monitoring and recording brain activity and/or providing brain stimulation, it will be appreciated that the implanted system 10 may also be used to monitor and record physiological signals from, or provide treatment therapies to, other locations of the body. The IMD 20 could, for example, be a neurostimulator device, a pacing device, a defibrillation device, an implantable loop recorder, a hemodynamic monitor that does not provide a pacing therapy, or any other implantable signal recording device known in the art or developed in the future. In FIG. 1, the IMD 20 is electrically coupled to the brain B of patient 12 through electrodes 30 and lead conductor(s) of at least one lead 19 in a manner known in the art. The electrodes 30 may also serve as therapy delivery elements to treat nervous system disorders. The IMD 20 may continuously or intermittently communicate with an external programmer 23 (e.g., patient or physician programmer) via telemetry using, for example, antenna 24 to relay radio-frequency signals 22, 26 between IMD 20 and programmer 23. In this embodiment, each of the features and functionalities discussed herein are provided by the IMD 20.

Those skilled in the art will appreciate that some medical device systems may take any number of forms from being fully implanted to being mostly external and can provide treatment therapy to any number of locations in the body, as disclosed in U.S. Pat. No. 6,341,236 (Osorio, et al.), incorporated herein by reference. For example, the medical device systems described herein may be utilized to provide treatment therapy including, for example, electrical stimulation, magnetic stimulation, and/or drug infusion. Moreover, it will be appreciated that the medical device systems may be utilized to analyze and treat any number of nervous system disorders. In the event that closed-loop feedback control is provided, the medical device system can be configured to receive any number of neurological signals that carry information about a symptom or a condition or a nervous system disorder. Such signals may be provided using one or more monitoring elements such as monitoring electrodes or sensors. For example, U.S. Pat. No. 6,227,203 provides examples of various types of sensors that may be used to detect a symptom or a condition or a nervous system disorder and responsively generate a neurological signal and is hereby incorporated by reference in relevant part.

Figure 2:
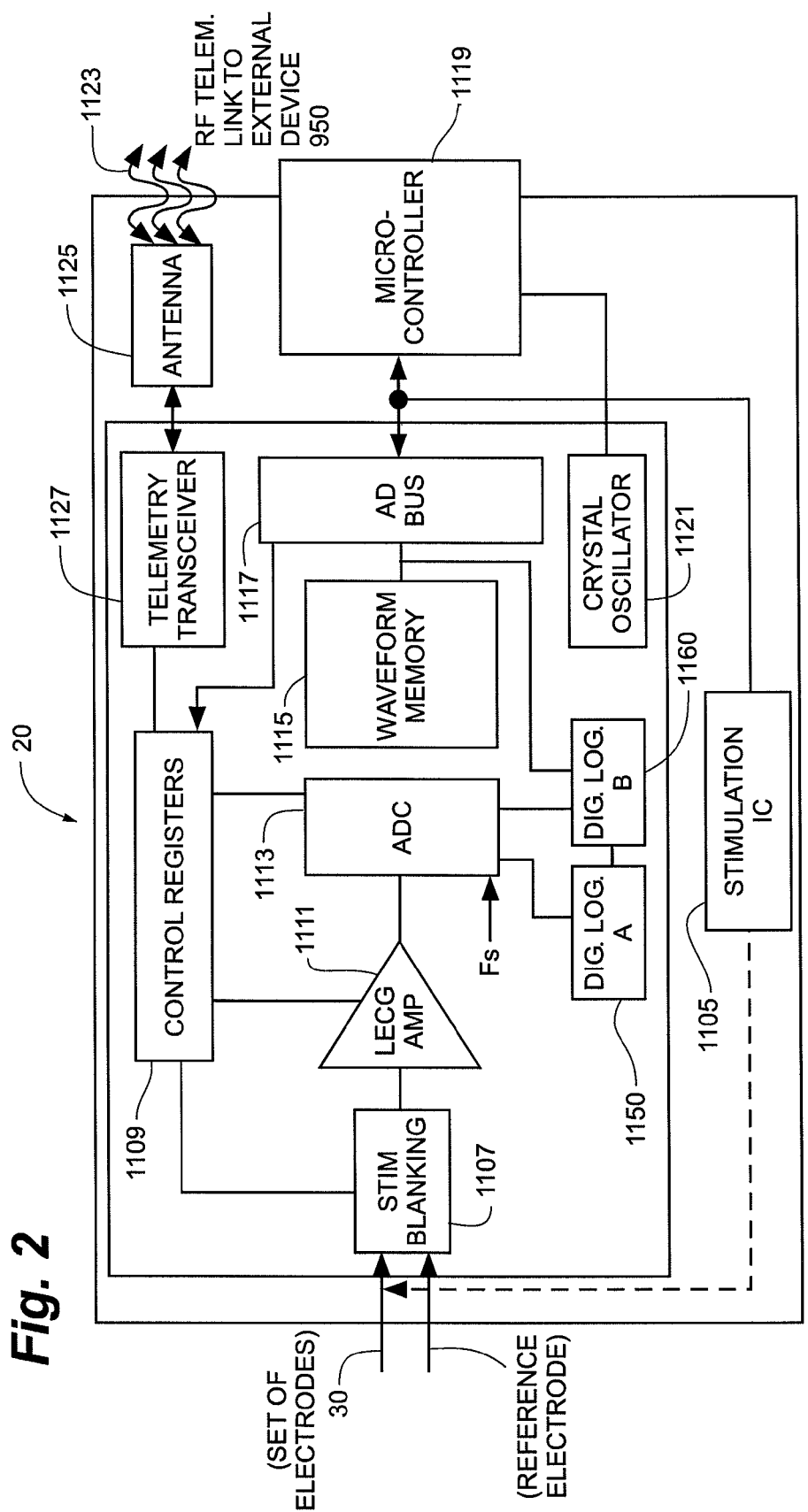
FIG. 2 is a schematic block diagram of an implantable medical device for treatment of a nervous system disorder in accordance with embodiments of the invention.

FIG. 2 is a schematic block diagram of an IMD 20. The IMD 20 is implanted in conjunction with a set of electrodes 30. The IMD 20 communicates with an external device, such as programmer 23 (FIG. 1), through a telemetry transceiver 1127, an antenna 1125, and a telemetry link 1123. The external device may collect data from the IMD 20 by placing antenna 24 on the patient's body 12 over the IMD 20 to thereby communicate with antenna 1125 of the IMD 20.

IMD 20 may contain an operating system that may employ a microcomputer or a digital state machine for sensing and analyzing physiological signals in accordance with a programmed operating mode. The IMD 20 may also contain sense amplifiers for detecting signals, and output circuits for delivering electrical stimulation therapy, for example, to certain parts of the brain B. The operating system may include a storage device for storing sensed physiological signals, including those associated with neurological activity. The storage device may also be used for storing operating parameters and other operating history data.

Each electrode of the set of electrodes 30 may be adapted to either receive a physiological signal, such as a neurological signal, or to stimulate surrounding tissue, or to perform both functions. Stimulation of any of the electrodes contained in the electrode set 1101 is generated by a stimulation IC 1105, as instructed by a microprocessor 1119. When stimulation is generated through an electrode, the electrode may be blanked by a blanking circuit 1107 so that a physiological signal is not received by channel electronics (e.g., amplifier 1111). U.S. Patent Application Publication 2004/0133248 to Frei et al. ("Channel-Selective Blanking for a Medical Device System"), incorporated by reference herein, discloses a method of blanking signal channels during the delivery of therapy. When microprocessor 1119 determines that a channel is able to receive a physiological signal, an analog to digital converter (ADC) 1113 samples the physiological signal at a desired rate (e.g., 250 times per second). Digital logic circuitry, indicated in FIG. 2 by digital logic 1150 and 1160, may be employed to receive the digitized physiological signal from ADC 113. The digitized physiological signal may be stored in a waveform memory 1115 so that the neurological data may be retrieved from the IMD 20 when instructed, or may be processed by microprocessor 1119 to generate any required stimulation signal. In some embodiments, digital logic 1150, 1160 may employ a data compression step, such as applying the new turning point (NTP) algorithm or other suitable algorithms or filters, to thereby reduce memory constraints that may be imposed on an IMD due to issues of size, power consumption, and cost, for example.

Figure 3:
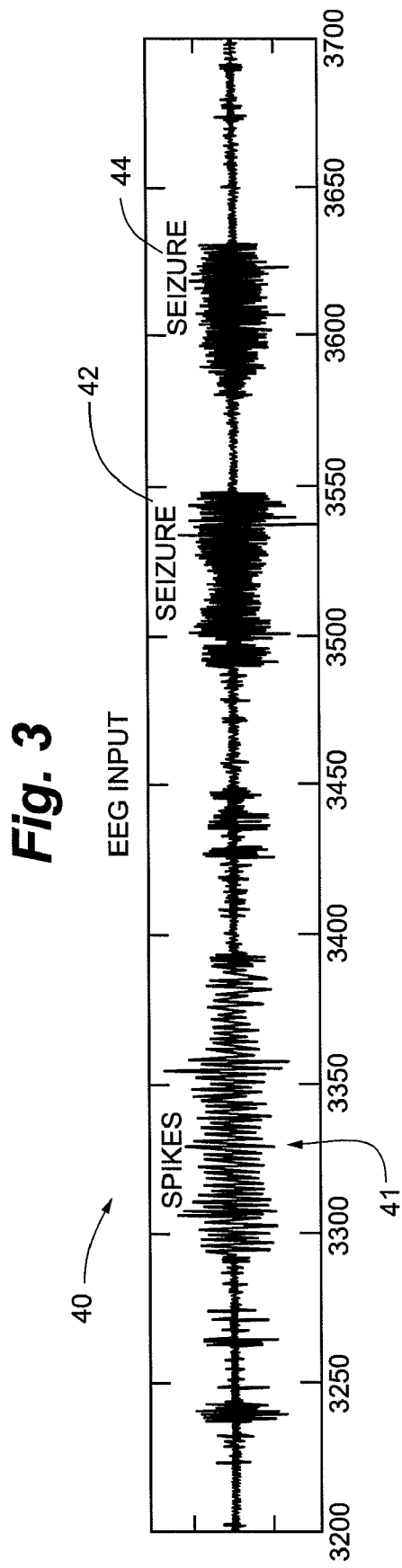
FIG. 3 is an exemplary EEG waveform, showing the onset of neurological events corresponding to epileptic seizures.

FIG. 3 shows an example of an EEG waveform 40. Epileptic seizures 42, 44 may manifest as changes in EEG signal amplitude energy, and/or frequency from an underlying EEG rhythm, as shown in FIG. 3. Also shown are epileptiform discharge spikes 41, which may occur prior to the occurrence of seizures 42, 44. In certain cases, neurological events, such as seizures 42 and 44, may be thought of as belonging to a single group or cluster of events, for example. Associating a group of events as belonging to a single cluster may, for example, be useful in making decisions regarding therapy delivery.

Figure 4:
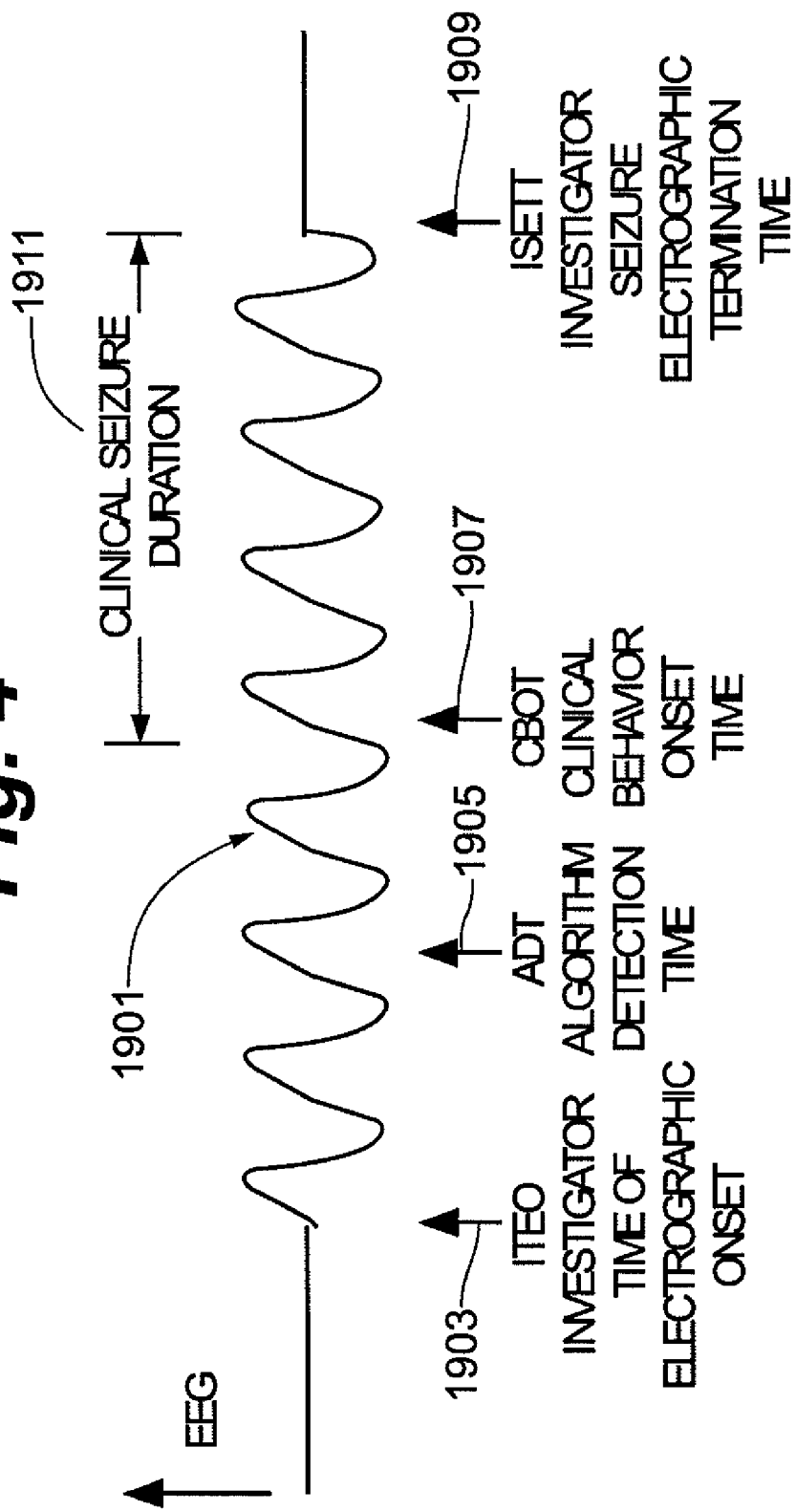
FIG. 4 shows a simulated EEG waveform, designating portions of a neurological event.

FIG. 4 shows a simulated EEG waveform 1901, designating portions of an exemplary neurological event. A time event 1903 corresponds to an investigator time of electrographic onset (ITEO), in which a clinician may observe a significant amount of electrographic activity on an EEG waveform 1901 that may mark the beginning of a neurological event such as a seizure. (However, a neurological event may not necessarily follow time event 1903 in some cases.) A time event 1905 corresponds to an algorithm detection time (ADT), in which a detection algorithm detects an occurrence of a neurological event based on processing of an EEG waveform 1901.

A time event 1907 corresponds to a clinical behavior onset time (CBOT), in which a patient typically manifests the symptoms of a neurological event (such as demonstrating the physical characteristics of a seizure). However, in some cases, a patient may not manifest symptoms even though an ITEO occurs. Typically, if monitoring elements (such as electrodes) are appropriately positioned, the CBOT 1907 will occur after the ITEO 1903. However, depending on the placement of the electrodes relative to the location of the neurological event, the CBOT 1907 may occur before the ITEO 1903 due to potential delays of neurological signals propagating through various portions of a patient's brain. A time event 1909 corresponds to an investigator seizure electrographic termination time (ISETT), in which the electrographic activity decreases to a level low enough to indicate termination of seizure activity. A time event 1911 is also provided in FIG. 4 to indicate clinical seizure duration, which may be defined as the time interval from CBOT 1907 to ISETT 1909.

Overview of IMD System

Figure 5:
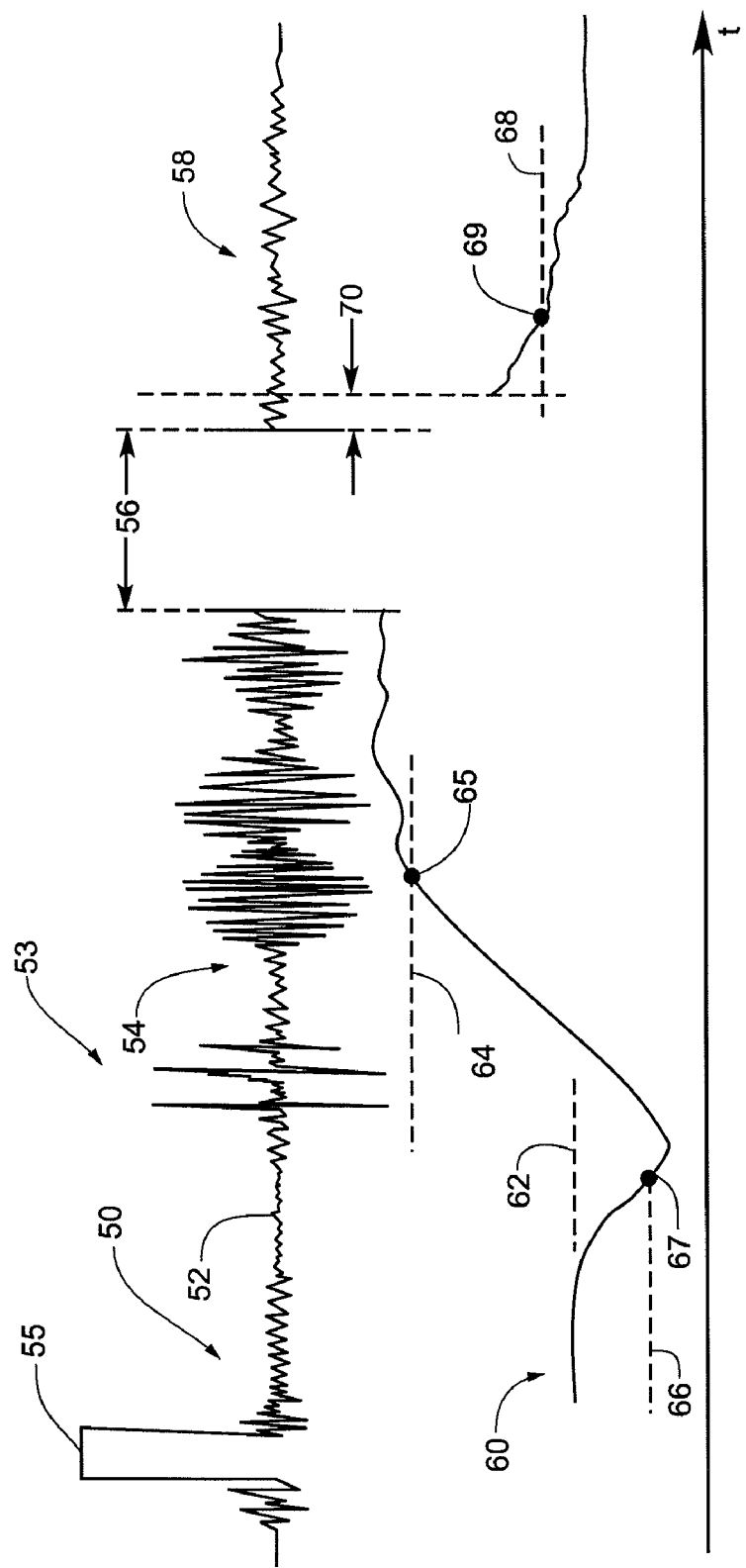
FIG. 5 shows an example of an EEG waveform and a plot of an exemplary event monitoring parameter for detecting neurological events in accordance with various embodiments of the invention.

FIG. 5 shows a time plot that generally illustrates the operation of an IMD system in response to an EEG signal in accordance with certain embodiments of the invention. A single channel EEG signal 50 is shown in the top plot spanning a period of time that includes pre-seizure activity, seizure onset, therapy delivery, and post-therapy monitoring of EEG signal 50. The bottom plot is an exemplary event monitoring parameter 60 that may be derived from one or more channels of EEG signals 50. The event monitoring parameter may also be referred to as a seizure monitoring parameter. FIG. 5 shows event monitoring parameter 60 starting from a relatively stable or normal value 62, corresponding to normal EEG signal activity or signal energies (e.g., during interictal periods). As shown, parameter 60 may increase or decrease due to changes in signal energy, and may cross one or more pre-defined threshold values 64, 66 to indicate the onset (or potential onset) of an epileptic seizure. Parameter 60 is shown crossing threshold 64 at point 65 to indicate the onset of an epileptic seizure 54, in this case identified by an increase in parameter 60 above a seizure onset threshold 64. In some embodiments, a seizure detection algorithm may also require the parameter 60 to exceed the threshold 64 for a specified duration (not shown) in order for the IMD to "detect" the seizure.

Similarly, parameter 60 is also shown dropping below threshold 66 at point 67 in FIG. 5 to indicate the possible onset of a seizure according to certain optional embodiments of the invention. A specified duration parameter may also be required to be met in order to detect a seizure based on this type of threshold criterion. As shown, a low-level threshold such as threshold 66 may be used to indicate a low level of EEG signal energy, as shown at 52, which may be used as an early predictor or precursor of an epileptic seizure in some embodiments of the invention.

The EEG signal 50 in FIG. 5 also shows epileptiform discharge spikes 53, which may also serve as an early predictor or precursor of an epileptic seizure. Certain embodiments of the invention include a method (not shown) for analyzing the occurrence of such spikes 53 and using them to "detect" (i.e., identify a precursor to) a possible seizure.

The methods of detecting seizures and seizure precursors described herein may be affected by the quality of the signals employed by the various methods. For example, periods of signal saturation or clipping, as indicated in EEG signal 50 at points 55, may provide false information to a seizure detection algorithm. Systems and methods for monitoring and accounting for signal quality are disclosed in U.S. Patent Application Publications 2004/0138580 and 2004/0138581 to Frei et al. (both entitled "Signal Quality Monitoring and Control for a Medical Device System"), both of which are hereby incorporated by reference in their respective entireties.

FIG. 5 also illustrates the delivery of therapy 56 from an IMD system in response to a detected seizure. The IMD system may provide therapy in the form of electrical stimulation to portions of the nervous system, or in the form of drug delivery, or in other forms of therapy suitable for the treatment of an epileptic seizure. FIG. 5 further illustrates the resumption of EEG signal monitoring following the delivery of therapy 56 to a patient, as shown in the EEG signal at 58. After successful therapy delivery by the IMD system, parameter 60 may drop below a seizure termination threshold 68 as shown at point 69, for a predetermined period of time in certain embodiments (e.g., a predefined duration).

An additional or optional aspect of an IMD in accordance with various embodiments of the invention is also indicated by post-stimulation interval 70 in FIG. 5. For example, at the termination of therapy 56, the IMD may not immediately have data available from which to derive or calculate parameter 60 (or data may be "old" data received prior to stimulation therapy, for example). In some embodiments, this may be at least temporarily addressed by an alternate means of determining parameter 60 (or a substitute parameter) after the delivery of therapy 56, which may quickly assess whether a seizure is still on-going and/or determine the need for additional stimulation therapy, for example.

Figure 6:
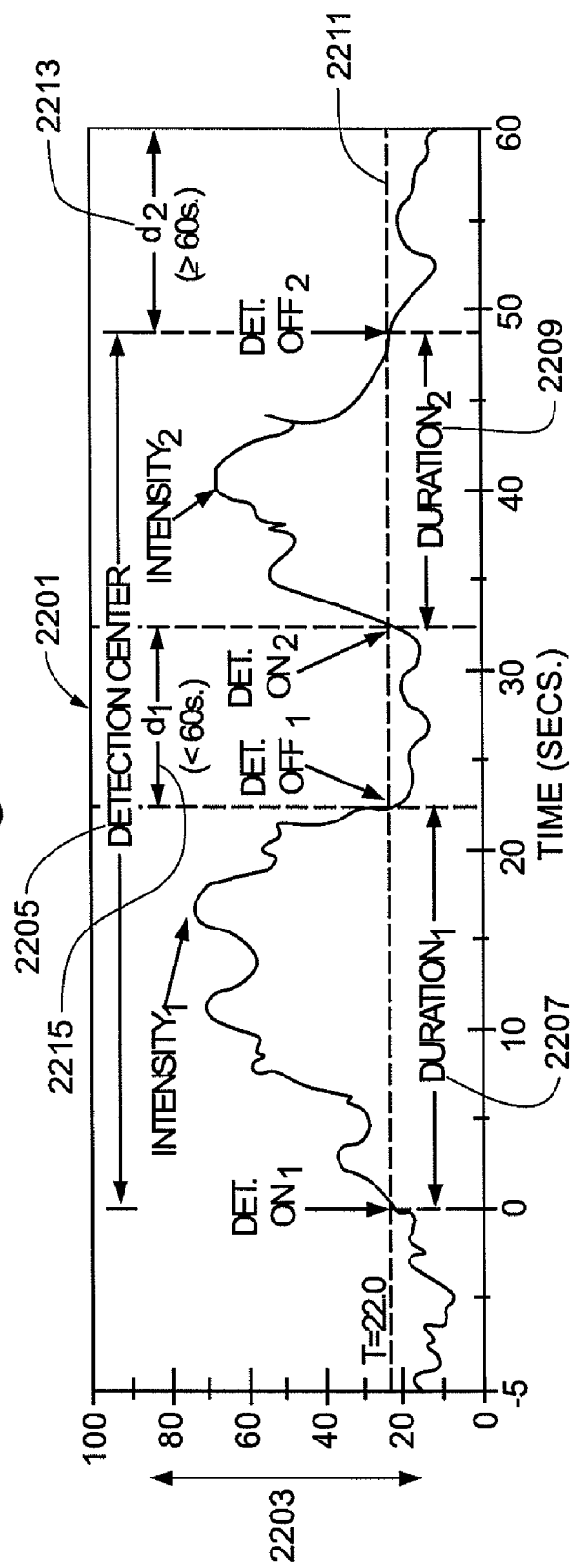
FIG. 6 is a plot of an exemplary event monitoring parameter associated with a seizure detection algorithm.

FIG. 6 shows a pair of neurological events detected using a method in accordance with certain embodiments of the invention. During a neurological event (such as a seizure), EEG activity, as monitored with a seizure detection algorithm, may result in multiple closely-spaced detections or clusters that a physician/clinician may wish to interpret as being related as part of a single event (e.g., one episode), and which, if considered as separate events, may result in an unnecessary therapy delivery, or possibly an unsafe number of therapy deliveries. This may be particularly true at the beginning or end of a neurological event when oscillations around the detection threshold may result in multiple closely-spaced detections, which may complicate operations and logging of events.

A medical device system, e.g., IMD 20, may associate clusters of closely-spaced detections using a temporal criterion. For example, detections that are separated in time by less than a programmable inter-detection interval may be classified as being related, and/or may be deemed to be part of the same cluster or episode. Parameters, such as an inter-detection interval, may be programmable in IMD 20, for example. U.S. Patent Application Publication 2004/0138536 to Frei et al. ("Clustering of Neurological Activity to Determine Length of a Neurological Event"), hereby incorporated by reference in its entirety, discloses such a method of detecting a cluster or clusters of neurological events.

FIG. 6 shows data 2201 associated with an event monitoring parameter 2203, which may be determined by a seizure detection algorithm. A pair of detections is shown, including two periods (duration1, at 2207, and duration2, at 2209) during which event monitoring parameter 2203 exceeds a threshold 2211, as well as a relatively brief intervening period, d1, between 2207 and 2209. Event monitoring parameter 2203 is displayed in FIG. 6 from about 5 seconds before the onset of the first detection to about 12 seconds after the end of the second detection. A number of methods of determining event monitoring parameter 2203 from one or more EEG signals are described below in later sections.

In certain embodiments, a time constraint may be defined such that, if event monitoring parameter 2203 falls below predetermined threshold 2211, then subsequently rises above predetermined threshold 2211 (e.g., a second detection occurs) within the defined time constraint, then that subsequent detection is considered to be related to the first detection (e.g., part of the same detection cluster). Thus, the pair of detections 2205 includes first duration 2207, the intervening interval, d1, and second duration 2209. Analysis of the event monitoring parameter 2203 may therefore be performed on clusters or groups of detections, rather than solely on individual detected events.

Seizure severity metrics (e.g., measures of the intensity of a detected seizure) may be based on analysis of the event monitoring parameter 2203 over an entire cluster 2205 (rather than on individual detected events), according to certain embodiments of the invention. For example, a severity metric may be defined as the maximum value of event monitoring parameter 2203 reached during cluster 2205 in certain embodiments. U.S. Patent Application Publication 2004/0133119 to Osorio et al. ("Scoring of Sensed Neurological Signals for use with a Medical Device System"), hereby incorporated by reference in its entirety, discloses such a method of scoring the severity of sensed neurological signals.

Referring again to FIG. 2, ADC circuit 1113 receives the filtered, amplified physiological signal from electrodes 30, which, in certain embodiments, may be sampled at appropriate rates, such as about 256 or 128 Hz or samples per second. Sampling physiological signals at rates above about 128 Hz is usually adequate to avoid "aliasing" because there is typically little energy above 60 Hz included in the sampled signal. "Aliasing" is a phenomenon of the digitization process that may be caused by sampling at too low a sample rate for a given signal, resulting in reproduced signals with spurious or erroneous frequency content. Aliasing is typically avoided by performing analog low-pass filtering prior to digitization to limit the frequency content, then sampling at a rate greater than about twice the frequency of the highest frequency content in the filtered signal. For example, the upper frequency corner of the analog filter should be no more than half of the sample rate (by Nyquist's Law), and is usually lower than that.

Data signals stored by the IMD 20 may be transmitted between an IMD RF telemetry antenna 1125 (FIG. 2) and an external RF telemetry antenna 24 associated with the external programmer 23 (FIG. 1). In an uplink telemetry transmission 22, the external RF telemetry antenna 24 operates as a telemetry receiver antenna, and the IMD RF telemetry antenna 1125 operates as a telemetry transmitter antenna. Conversely, in a downlink telemetry transmission 26, the external RF telemetry antenna 24 operates as a telemetry transmitter antenna, and the IMD RF telemetry antenna 1125 operates as a telemetry receiver antenna. Both RF telemetry antennas 24 and 1125 are coupled to a transceiver including a transmitter and a receiver. This is as described in commonly-assigned U.S. Pat. No. 4,556,063, herein incorporated by reference in relevant part.

Implantable Seizure Detection Algorithm

As noted above with respect to FIG. 5, an event monitoring parameter 60 may be derived from one or more EEG signals to form the basis of a seizure detection algorithm. Several event monitoring parameters 60 may be derived and used concurrently in certain embodiments, for example, by combining several such parameters using logical functions (e.g., AND, OR, MAX, MIN, etc.). In the sections that follow, a ratio method and an evidence counter method are described, either or both of which may be used by an IMD to detect the onset of neurological events such as seizures. Several methods are also described below which may anticipate or predict neurological events, for example, by detecting one or more precursors of seizure activity.

I. Seizure Detection—Ratio Method

Adverse neurological events, such as epileptic seizures, are typically characterized by increases in EEG signal energy (including increases in signal amplitude and/or frequency). An increase in EEG signal energy (e.g., within a specified frequency range) may be identified or detected, for example, relative to a reference or background level of EEG signal energy. An event monitoring parameter may therefore be defined as a ratio of a relatively recent, short-term representation of an EEG signal (e.g., the "foreground" of "FG") to a relatively long-term representation of an EEG signal (e.g. the "background" or "BG"). The short-term and long-term representations may be indicative of EEG signal amplitude, energy, and/or frequency, according to various embodiments of the invention.

The foreground may, for example, be determined from analysis of an EEG signal acquired over a first sample interval. The first sample interval may be a relatively recent, relatively brief time window in certain embodiments of the invention. In one particular embodiment, a recent two-second time window may be used as the first sample interval for calculating the foreground. In certain embodiments, a median value of the EEG signal magnitude over the two-second window may be used as the foreground. Of course, shorter or longer time windows can be chosen from which to base the determination of the foreground, as would be apparent to one of ordinary skill in the art. Similarly, statistical measures other than the median (e.g., mean, root-mean-square, weighted averages, etc.) may be used to determine a value for the foreground.

A relatively long-term representation of the EEG signal (e.g., the background) may be derived from EEG signal data values accumulated over a second sample interval spanning a relatively long period of time (i.e., longer than the first sample interval). For example, a 20-minute or 30-minute period may be appropriate for the second sample interval according to some embodiments. In certain embodiments, a median value of the EEG signal magnitude over the 20- or 30-minute period may be used as the background. Of course, longer or shorter periods may also be used. Similarly, statistical measures other than the median may also be used to determine a value for the background.

Figure 7:
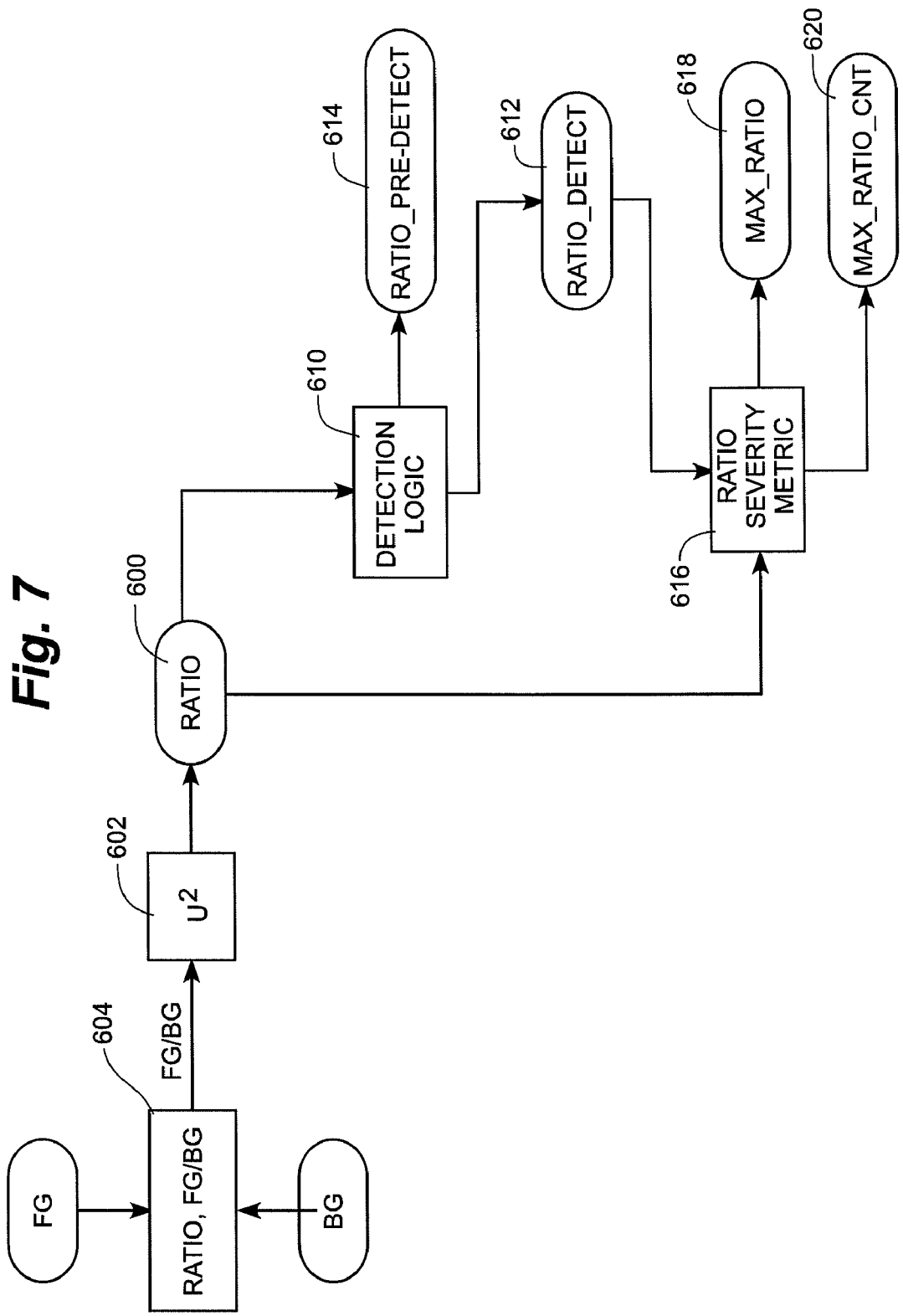
FIG. 7 is a block diagram showing a method of detecting a neurological event according to an embodiment of the invention.

As mentioned above, a ratio of foreground and background signal energies may be defined and used as a criterion for detecting neurological events, such as epileptic seizures. FIG. 7 illustrates one possible embodiment of the invention in which a ratio 600 is computed from the above-described foreground and background signals, FG and BG. In the embodiment shown, the ratio may be determined by dividing the foreground FG by the background BG at function 604, then optionally squaring the result as shown by the squaring function, $U^2$ 602 to produce ratio 600. In certain embodiments, the foreground and background signals, FG and BG, may each be squared (by a function similar to function 602) prior to forming the ratio 600. As would be apparent to one of ordinary skill in the art, other similar functions may be used to determine ratio 600. For example, the optional squaring function 602 may be omitted and/or replaced with other functions, such as an absolute value function, or a difference function, or a squared difference function, or combinations of these and other functions.

In certain embodiments of the invention, determining the value of ratio 600 may be performed by a method that estimates the ratio using an exponential approximation technique substantially as described in commonly assigned U.S. patent application Ser. No. 10/976,474. According to this technique, a ratio of a numerator (e.g., the short-term representation) to a denominator (e.g., the long-term representation) may be estimated by raising the number 2 to an exponent value, the exponent value being equal to the difference in the most significant set bit (MSSB) positions of the denominator and numerator, respectively. The MSSB position may be defined as the numbered bit position of a first non-zero bit in a binary number, starting from the most significant bit (MSB) of that number. For example, the exponent value may be obtained by determining the difference between the MSSB position of the long-term representation and the MSSB position of the short-term representation. The following example illustrates the use of this technique.

Numerator: 01000011 (equals 67 in decimal notation)
Denominator: 00010001 (equals 17 in decimal notation)

The MSSB of the numerator is 2, since the second bit position holds the first non-zero bit, starting from the MSB (left-most bit). The MSSB of the denominator is 4, since the fourth bit position holds the first non-zero bit, starting from the MSB. Applying the technique, an estimate of the ratio of the numerator to the denominator is obtained by raising 2 to an exponent value equal to 4−2 (=2). Thus, the estimate is $2^2=4$, which is reasonably close to the value of 67/17. Of course, various refinements and minor modifications to the technique described may be employed by one of ordinary skill in the art to determine a ratio value in accordance with embodiments of the invention, and would be considered to fall within the scope of the invention as claimed.

The onset of a neurological event (e.g., a seizure) may be detected when a predefined ratio 600 of foreground and background signal levels (or a function derived therefrom) crosses or exceeds an onset threshold. In certain embodiments, detection of a seizure may further require that the ratio 600 exceed the threshold for a specified period of time (e.g., duration), according to certain embodiments of the invention. This is shown as detection logic 610 in FIG. 7. Seizure detection logic 610 may further include a seizure termination threshold and optionally a seizure termination duration parameter which may be used to indicate the end of a seizure episode, for example, when the ratio 600 falls below the termination threshold for a period longer than the termination duration. The threshold and duration parameters may be pre-defined and/or user-selectable, and need not be the same for onset and termination.

FIG. 7 also shows the output of detection logic 610 as including two possible outputs, RATIO_DETECT 612 and RATIO_PRE_DETECT 614. RATIO_PRE_DETECT 614 may change from a logical value of "False" (e.g., a value of 0) to a logical value of "True" (e.g., a value of 1) when the ratio 600 first exceeds the onset threshold, for example. If the ratio 600 exceeds the onset threshold for the onset duration, the RATIO_DETECT 612 value may also change from a logical value of "False" (e.g., a value of 0) to a logical value of "True" (e.g., a value of 1). RATIO_DETECT 612 and RATIO_PRE_DETECT 614 may both return to "False" (e.g., a value of 0) if the ratio 600 falls below a predetermined termination threshold. Some embodiments may also require that the ratio 600 remain below the termination threshold for a predetermined duration before assigning a logical value of "False" to the RATIO_DETECT 612 and RATIO_PRE_DETECT 614.

In embodiments using a duration parameter, either for the onset threshold or the termination threshold, duration may be defined in a number of ways. For example, to satisfy the duration parameter, the method may require that a specified number of consecutive ratio 600 values exceed the threshold value before the duration is satisfied. Alternately, the duration parameter may be defined to require that consecutive ratio values meet the respective threshold criteria for a specified period of time. In other embodiments, the duration parameter may be defined such that duration is satisfied, for example, by having at least a certain number of ratio values within a predefined window of ratio values that exceed the respective threshold values (e.g., a predetermined percentage of values of the ratio must exceed the threshold for over the given duration parameter). For example, a duration criterion may require that seven out of a rolling window of ten ratio values exceed the respective threshold value in order to satisfy the duration criterion. Other possibilities exist for devising a duration criterion, as would be apparent to one of ordinary skill in the art with the benefit of these teachings.

The use of a ratio parameter 600 as a detection criterion may typically detect seizures a few seconds after the electrographic onset. It is hypothesized that therapy effectiveness may diminish the longer therapy is delayed from onset. Therefore, to minimize the delay between detection of a seizure and delivery of therapy (e.g., electrical stimulation), the output stimulus circuits in an IMD may be adapted to begin charging prior to seizure detection. For example, the output stimulus circuits may receive instructions to begin charging when RATIO_PRE_DETECT 614 becomes True (e.g., a logical value of 1) in embodiments where this marks the beginning of a duration criteria. Thus, the output stimulus circuits may have time to become at least partially charged prior to satisfying a seizure onset duration parameter, according to some embodiments of the invention. This may, for example, allow enough time for the stimulus circuits to become fully charged and ready to deliver stimulation therapy immediately after duration is satisfied and/or RATIO_DETECT 612 becomes "True."

The ratio parameter 600 may also be used to determine whether a group of detected neurological events are related, for example, as part of a single seizure cluster or episode. For example, a given neurological event may be considered to be part of the same seizure cluster or episode as the immediately preceding neurological event if the amount of time that elapses from the end of the immediately preceding neurological event to the given neurological event is less than a predefined cluster timeout interval.

II. Seizure Detection—Evidence Count Method

In certain embodiments of the invention, an alternate method of detecting neurological events such as seizures may be employed, either alone or in combination with other methods such as the ratio method described above. Thus, an event monitoring parameter may be defined using an "evidence count" technique, as described below.

Figure 8:
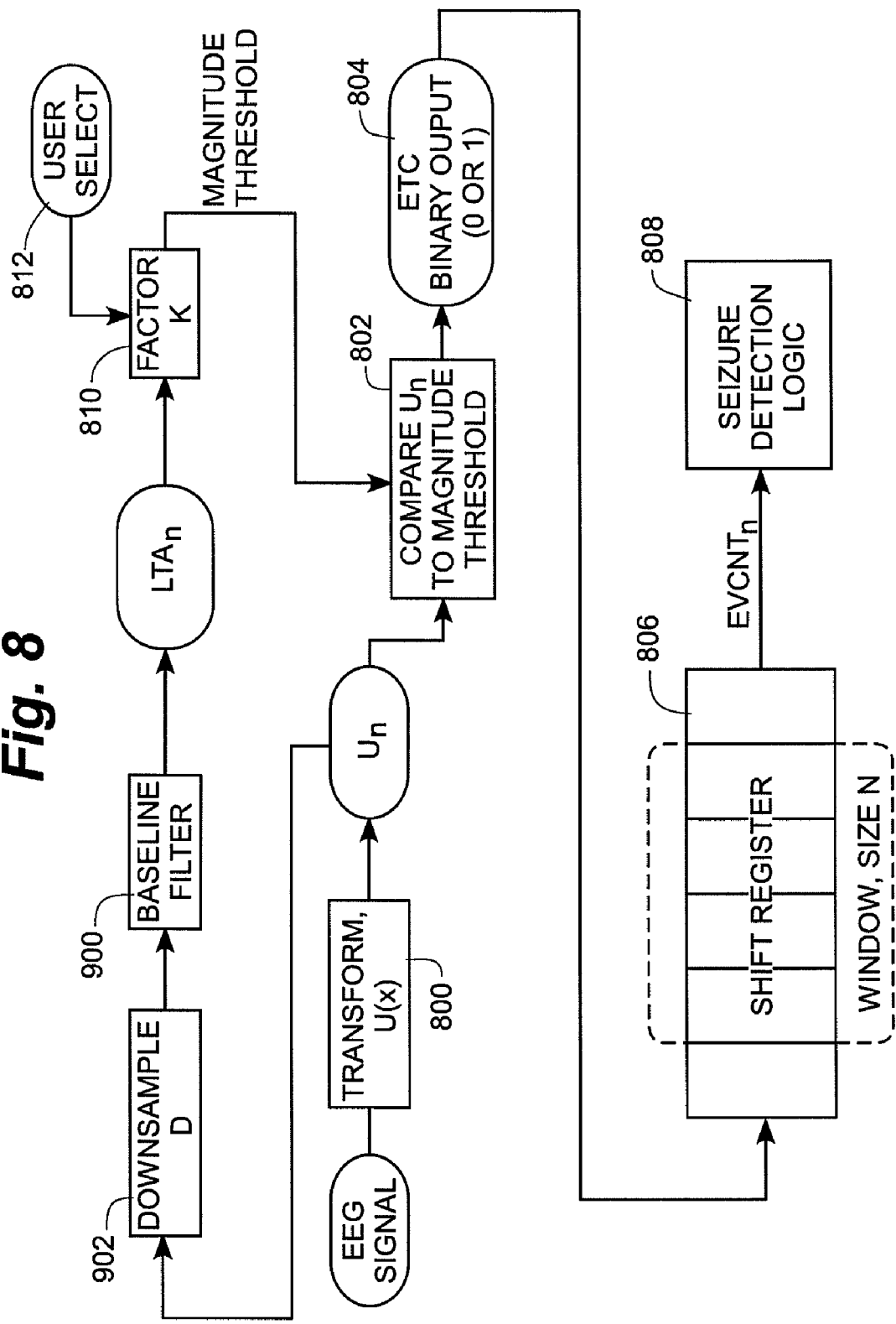
FIG. 8 is a block diagram of a method of detecting a neurological event according to an embodiment of the invention.

As shown in FIG. 8, an input stream of EEG sampled data values (e.g., obtained by sampling an EEG signal at a sample rate) are applied to a signal transform function, U(x) 800, which generates a transformed signal comprising a stream of data magnitudes values, $U_n$. Examples of signal transform functions 800 may include, but are not limited to, an absolute value function, a difference signal (e.g., the magnitude of the difference between successive input data signals), the square of the input magnitude, the square of the difference signal, and combinations of these and other signal transform functions. Suitable signal transform functions may, for example, produce positive values derived from the stream of sampled data values. Each transformed data magnitude value, $U_n$, is then compared to a magnitude threshold at comparator 802. Comparator 802 produces a stream of comparator output values that indicate whether or not a given $U_n$ value exceeds the magnitude threshold value. The comparator 802 may produce a stream of comparator output values comprising a stream of binary values (e.g., 0's and 1's) to indicate the results of the evidence count threshold comparisons, ETC 804, which may then be input to a memory device 806 (e.g., a shift register, data stack, or FIFO buffer) for use in determining an event monitoring parameter.

An event monitoring parameter, $EVCNT_n$, may be calculated based on a rolling sum of the comparator output values (e.g., a rolling sum of the binary values from ETC 804) in a window/buffer of size N within memory device 806. The event monitoring parameter, $EVCNT_n$, may then be applied to seizure detection logic 808 in certain embodiments of the invention to detect a neurological event such as a seizure. The seizure detection logic 808 may, for example, incorporate the use of an onset threshold such that a neurological event is identified when the event monitoring parameter exceeds the onset threshold. Other aspects of seizure detection logic 808, such as the use of a termination threshold, or the use of a duration parameter for either or both thresholds, may also be used and would be comparable to that described above with respect to the ratio method.

The magnitude threshold used by the comparator may have a pre-defined value according to certain embodiments, or may be derived from a long-term representation of the EEG signal. A long-term representation of the EEG signal may be determined from the data magnitude values, $U_n$, by computing a long-term running average ("LTA") or other similar measures, including a low-pass statistic or an order statistic, for example without limitation. In certain embodiments, the magnitude threshold may be proportional to the long-term representation. For example, the long-term representation (e.g., LTA) may be multiplied by a seizure threshold factor to obtain the magnitude threshold value. With continued reference to FIG. 8, the magnitude threshold value that is compared to the $U_n$ data magnitude values at 802 may be obtained by multiplying the $LTA_n$ values by a seizure threshold factor, K, as shown at 810. In some embodiments, the seizure threshold factor could be a predetermined value ranging from about 2 to 64, and may be set to a nominal value of 22 in certain preferred embodiments. As shown at user select 812, the seizure threshold factor K may be optionally user-selectable in certain embodiments. A number of methods of determining a long-term representation, such as LTA, may be possible. One such method is described below with reference to FIG. 9.

Figure 9:
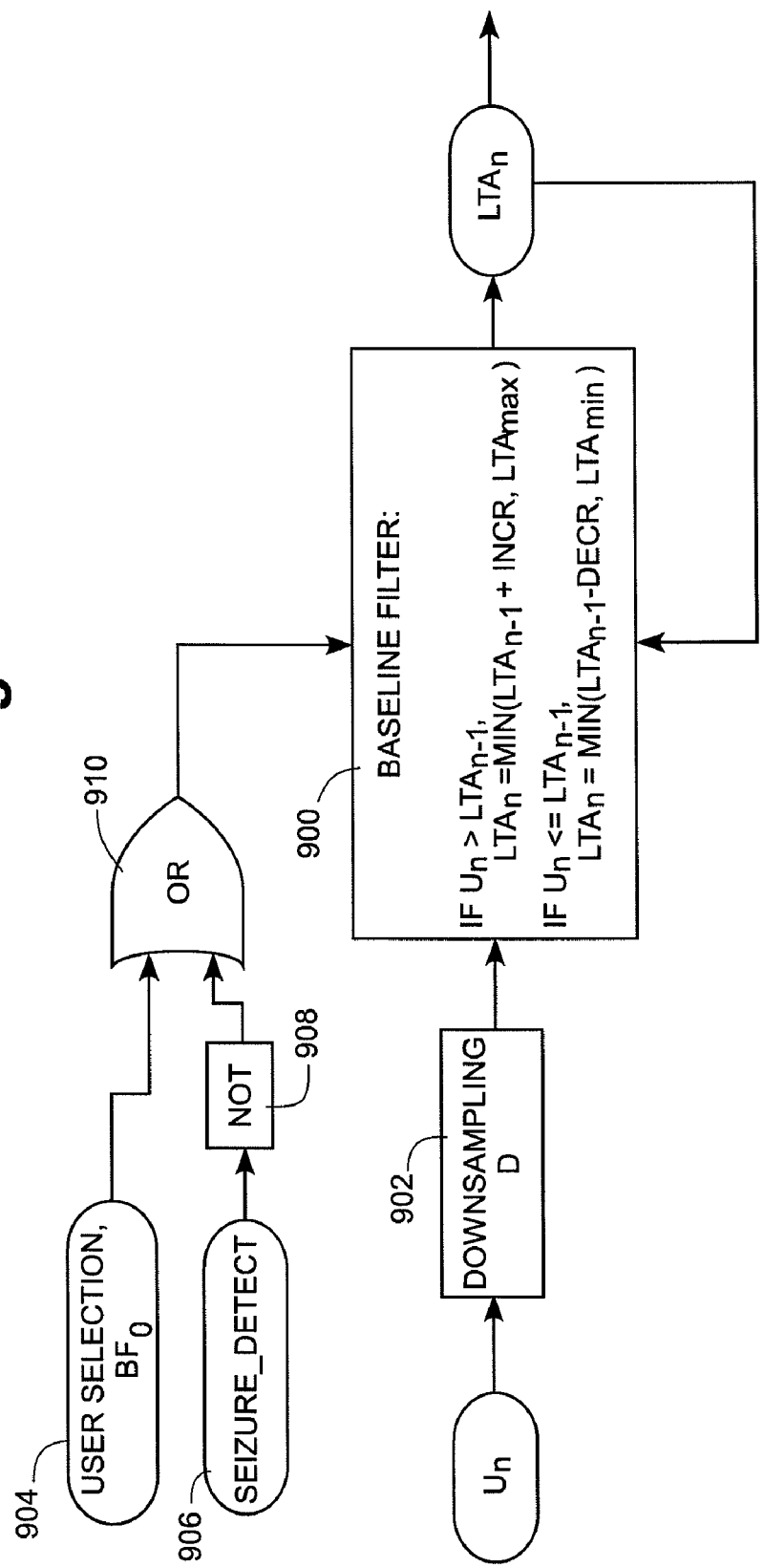
FIG. 9 is a block diagram showing a method of determining a parameter used in the method of FIG. 8.

FIG. 9 shows a method of determining LTA values for use with an evidence count seizure detection method (e.g., as the long-term representation of the EEG signal). In certain embodiments, the data magnitude values, $U_n$, may be used to calculate LTA by applying the $U_n$ values to a baseline filter 900. Baseline filter 900 may be a discrete integrator that compares each $U_n$ value to a previously determined value of LTA, and increments or decrements the value of LTA by a predetermined amount, depending on whether $U_n$ is greater than or less than the prior LTA value, respectively. In one particular embodiment, baseline filter 900 may also establish a maximum and/or a minimum value that may be obtained by the long-term representation (e.g., LTA). Such an embodiment may be expressed as follows:

If $U_n > [LTA_{n-1}]$, $LTA_n = \min(LTA_{n-1} + \Delta_{incr}, LTA_{max})$,
and If $U_n \leq [LTA_{n-1}]$, $LTA_n = \max(LTA_{n-1} - \Delta_{decr}, LTA_{min})$.

When both increment and decrement amounts, $\Delta_{incr}$ and $\Delta_{decr}$, are used, they need not be the same, although they may have the same value in certain embodiments.

A predetermined initial value of the long-term representation (e.g., $LTA_0$) may be provided, or may be selectable, to serve as an initial estimate of the long-term representation in some embodiments. In certain embodiments, the $U_n$ values applied to the baseline filter to determine the long-term representation may be selected by downsampling the $U_n$ values by a downsampling factor, D, as shown at 902, before being applied to baseline filter 900.

FIG. 9 also shows an alternate embodiment which may be used to disable the calculation of $LTA_n$ values, for example, during periods where a seizure has been detected and may still be in progress. (Continuing to calculate $LTA_n$ values during periods of seizure activity may cause the $LTA_n$ values to rise inappropriately, and may affect the ability of an IMD to detect subsequent seizure activity, for example.) FIG. 9 shows a logical "OR-gate" 910 supplying an input to baseline filter 900 that effectively acts as an ON/OFF switch for the baseline filter 900. In certain embodiments, a user selection, $BF_0$ (at 904), may be set to a logical value of "1" to ensure that the baseline filter 900 continues to determine to $LTA_n$ values regardless of the state of seizure detection. If instead, user selection $BF_0$ is set to 0, then the output of the OR-gate 910 (and hence, whether the baseline filter 900 calculates $LTA_n$ values) is determined by the status of seizure detection (e.g., by the logical outputs RATIO_DETECT and/or SEIZURE_DETECT), as shown at 906. A logical "NOT" function, 908, may be applied so that the determination of $LTA_n$ values by baseline filter 900 occurs only when a seizure detection (or detection cluster) is not in progress.

III. Seizure Precursor Detection—Level Crossing Method

In some embodiments of the invention, a method of identifying a "precursor" to a neurological event such as an epileptic seizure may use a "level crossing" technique that compares incoming EEG signals to one or more level thresholds (e.g., an upper and a lower level threshold) that define a number of amplitude ranges. The technique may keep track of crossings between amplitude ranges (e.g., transitions in EEG signal amplitude from one amplitude range to another). The number and/or frequency of such level crossings may be used to identify the occurrence of a precursor to seizure activity, such as the presence of epileptiform discharge spikes, for example, which may occur prior to the onset of an epileptic seizure. Epileptiform discharge activity may typically manifest as brief, sudden increases in the amplitude of EEG signals (e.g., spikes), and may have either positive or negative amplitudes.

The identification of precursors to seizures, rather than the seizures themselves, may allow more time for a device or system to prepare for a seizure (e.g., to allow time to charge stimulation circuitry needed for therapy delivery), or may allow for the delivery of preliminary therapy that may be able to prevent or lessen the severity of a subsequent seizure, for example. It has been shown that using such a level crossing technique may anticipate the occurrence of a seizure many seconds prior to the electrographic onset, and in some cases, a few minutes prior.

In certain embodiments, a method of detecting a precursor to a neurological event may include sampling an EEG signal to obtain a stream of data values, and applying the data values to a level transform (or clipper transform), which may include one or more level thresholds (e.g., an upper level and a lower level threshold) from which a number of amplitude ranges or zones can be defined. The level transform may be adapted to produce a stream of output values, each output value identifying the amplitude range corresponding to a given data value. In some embodiments, amplitude ranges may include the following: 1) signals below the lower level (e.g., below a pre-defined negative amplitude), 2) signals above the upper level (e.g., above a pre-defined positive amplitude), and 3) signals at or between the lower and upper levels. In some embodiments, a level transform may use a single level threshold to define two amplitude ranges. In such an embodiment, for example, an absolute value function may be incorporated so that data values are converted to positive values before being applied to such a level transform.

The output values produced by the level transform may next be applied to a change detector, which produces a stream of change signal values. For example, the change detector may produce a change signal value having a first value if a given output value (e.g., the "current" output value) is different from an immediately preceding output value. The change detector may produce a change signal value having a second value if a current output value is the same as an immediately preceding output value. A count of the first values would therefore provide an indication of the frequency of level crossings, and thus, may provide a method of detecting a precursor to a seizure event. The count of first values may be taken over a predefined window, which may be defined in terms of time or as a certain number of output values, for example. In some embodiments, the count of first values may be compared to a precursor threshold to detect a precursor to a seizure event, detection being based on the count exceeding a predefined precursor threshold, for example.

In certain embodiments, the number of level crossings (e.g., transitions of signal values from one amplitude range to another) that occur over a specified period of time may be used to define a "crossing count" value. A "rolling sum" of crossing count values may be used to define a "crossing trend" value, which can be used to identify a precursor to a seizure. For example, when the crossing trend value exceeds a predetermined threshold value (perhaps for a predetermined duration period), the identification of a seizure precursor may be said to occur.

In the example that follows, an embodiment of the invention is described which illustrates the use of a level crossing technique to identify a precursor to neurological events such as epileptic seizures. The example is meant to be illustrative in nature, as modifications of the technique described may be devised by one of ordinary skill in the art with the benefit of these teachings without departing from the scope of the invention as claimed.

Figure 10:
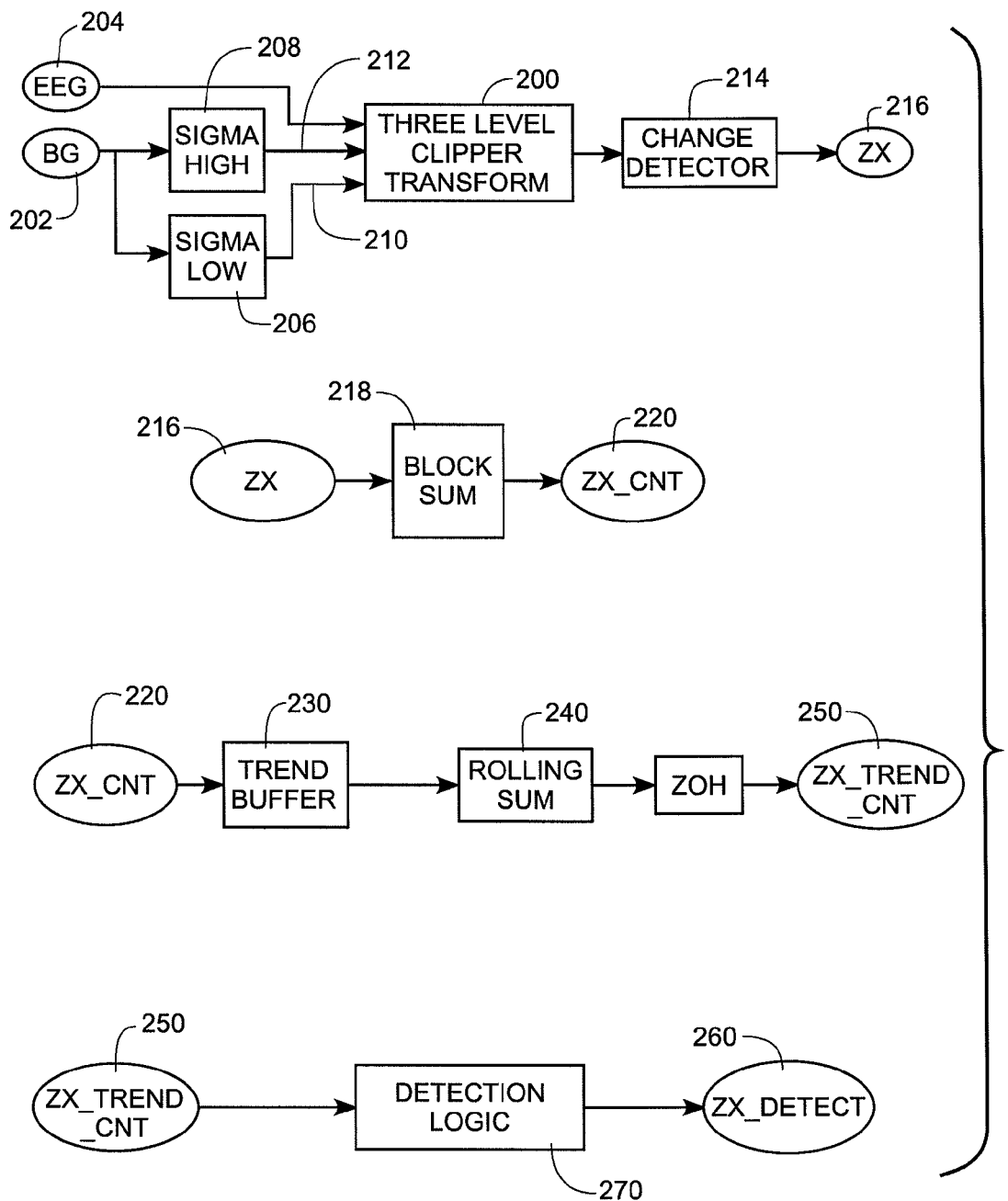
FIG. 10 is a block diagram showing a method of detecting a precursor to a neurological event according to an embodiment of the invention.

FIG. 10 is a block diagram that illustrates a level crossing technique in accordance with certain embodiments of the invention. In the embodiment illustrated, a level transform 200 produces an output having three possible values based on the input signals. The inputs may include a signal representative of long-term EEG signal levels, such as a background level signal 202 (e.g., the BG signal described above with respect to the ratio technique), and an EEG input signal 204. The long-term EEG signal level (e.g., background level signal 202) may, for example, be used to determine upper and lower level thresholds by determining multiples of the background level signal 202. Thus, the upper and lower thresholds may vary over time with changes in the background level, and the corresponding amplitude ranges determined by the upper and lower thresholds may be considered adaptive amplitude ranges, according to certain embodiments. This is shown in FIG. 10, as scale factors or multipliers 206 and 208, which are used to produce lower and upper level thresholds 210, 212, respectively, equal to multiples of the background level signal 202, for example. Of course, alternate means of determining values to use for the level thresholds 210, 212 in the level transform 200 may be devised, such as using various mathematical formulae and/or logic functions to derive the values, or simply using fixed values, or other techniques known in the art.

Having defined the upper and lower level thresholds 210, 212 the level transform 200 may be used to transform EEG input signal 204 into a stream of output values having three possible values, the output values identifying the amplitude range corresponding to each input data value, as described below:

Level transform output=1 if EEG signal 204>upper level threshold 212;

Level transform output=0 if EEG signal 204 is equal to or between level thresholds 210 and 212;

and

Level transform output=−1 if EEG signal 204<lower level threshold 210.

Of course, one of ordinary skill in the art would recognize that different numbers of level thresholds and/or amplitude ranges could be used without departing from the scope of the invention as claimed. For example, a single level threshold could be used to define two amplitude ranges according to certain embodiments of the invention. The values chosen for the level threshold(s), and hence the amplitude ranges, may also be varied (e.g., for a particular patient) so that they are adapted to identify epileptiform discharge activity and/or to differentiate epileptiform discharge spikes from normal EEG activity. Such variations would also be deemed to fall within the scope of the claimed invention.

Next, a level crossing (or level transition) may be defined as occurring when the level transform output changes value. This function is illustrated as change detector 214 in FIG. 10. A change detector 214 is adapted to produce a stream of change signal values (ZX) wherein a given change signal value, $ZX_n$, has a first value (e.g., 1) whenever the current level transform output value is different from the immediately preceding level transform output value, and has a second value (e.g., 0) whenever the level transform output value is the same as the immediately preceding value. In other words, $ZX_n$=1, if (Level transform)$_n$≠(Level transform)$_{n-1}$, and $ZX_n$=0, if (Level transform)$_n$=(Level transform)$_{n-1}$.

ZX is indicated at 216 in FIG. 10. Thus, a ZX value of 1 marks the occurrence of a transition in amplitude from one amplitude range to another. In certain embodiments, it may be desirable to define an additional value to account for large changes in amplitude. For example, in an embodiment where there are 3 amplitude ranges, a change signal value, $ZX_n$, might be assigned a value of 2 if the signal amplitude changes from the highest to the lowest amplitude range, or from the lowest to highest.

Next, a level crossing parameter, ZX_CNT 220, may be defined as being the number of level crossings or transitions over a specified period of time, or as the sum of the change signal values, ZX, over a window or block of N change signal values, according to some embodiments. For example:

ZX_CNT=$\Sigma ZX_n$ from $n$=1 to $n$=$N$.

In some embodiments of the invention, the windows or blocks of N samples used to derive the ZX_CNT parameter may be chosen to be non-overlapping such that each subsequent determination of ZX_CNT is based on a unique block of ZX data, as shown by block sum 218 and ZX_CNT 220 in FIG. 10.

Figure 11:
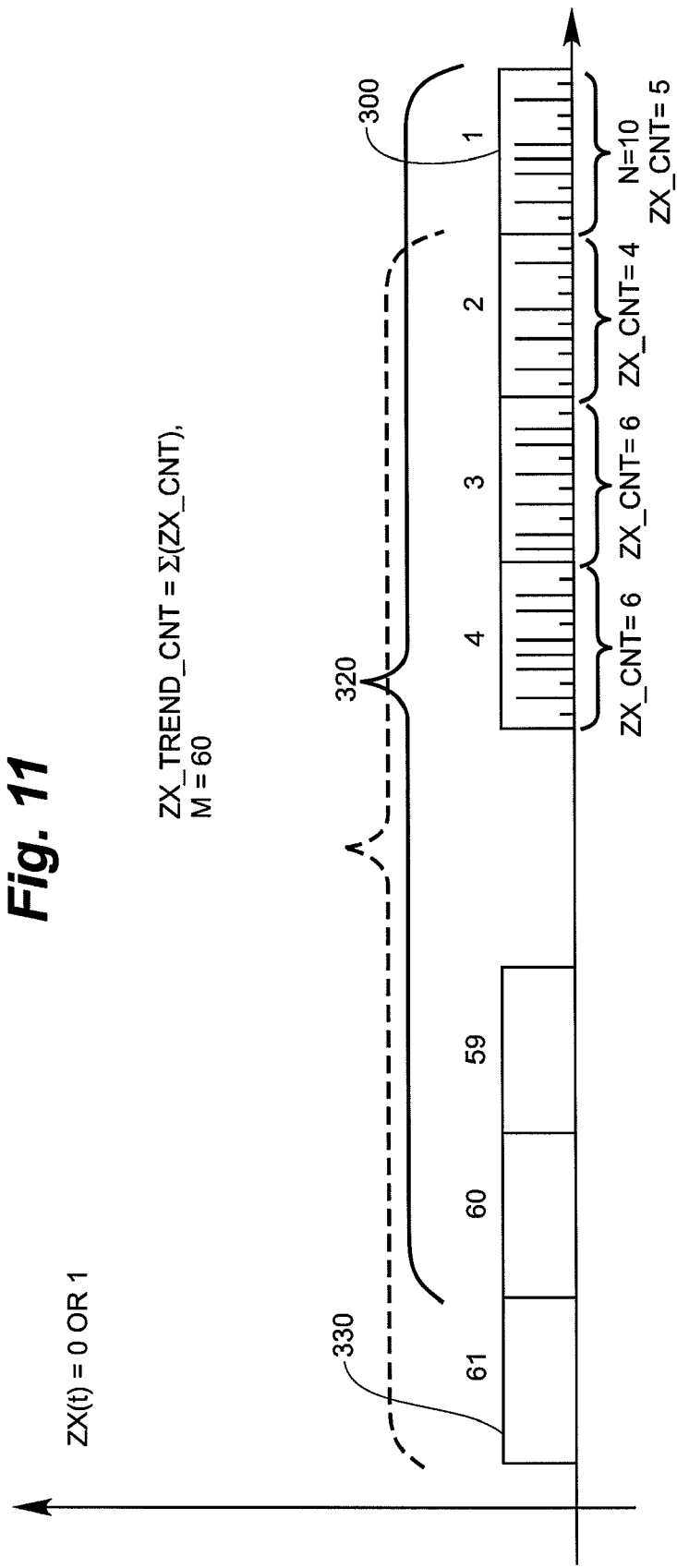
FIG. 11 is a timeline illustrating the determination of parameters used in the method of FIG. 10.

In certain embodiments, a rolling sum value of the ZX_CNT values from a certain number of windows or blocks of N samples may next be calculated to determine a level crossing precursor trend count, ZX_TREND_CNT 250, that updates with the determination of each new ZX_CNT value. This is illustrated in FIG. 11, which shows level crossings, ZX, plotted as a function of time. A block 300 of N samples is shown in which N=10 (e.g., 10 samples per block), and ZX_CNT=5 (e.g., 5 instances of ZX=1 and 5 instances of ZX=0 for a sum of 5). In the example shown, a rolling trend buffer 320 has M blocks of N samples each, where M=60 and N=10. The ZX_TREND_CNT value at a given point in time is the sum of the 60 ZX_CNT values in the trend buffer 320. As each new block of N samples is obtained and a new ZX_CNT value determined, the oldest block 300 is dropped from the trend buffer 320, and the newest block 330 is added, so that a new value of the precursor trend count, ZX_TREND_CNT, may be determined.

Referring again to FIG. 10, ZX_CNT 220 values are shown as inputs to a trend buffer 230, from which a rolling sum 240 is computed, substantially as described above with respect to FIG. 11, to obtain ZX_TREND_CNT 250. The ZX_TREND_CNT 250 value may next be applied as a monitoring parameter for identifying a precursor to a neurological event such as a seizure, for example, by comparing the ZX_TREND_CNT 250 value to a predetermined threshold value, which may be a part of detection logic 270 in FIG. 10. A neurological event precursor may be identified by the occurrence of the ZX_TREND_CNT 250 value exceeding the predetermined threshold value. In certain embodiments, the ZX_TREND_CNT 250 value must exceed the predetermined threshold value for a predetermined duration before a neurological event precursor is identified. Similarly, the termination of a seizure precursor episode may be defined by the occurrence of the ZX_TREND_CNT value decreasing below a predetermined termination threshold value, possibly for a predetermined termination duration. A level crossing detection output, ZX_DETECT 260, may also be defined, having a logical value of 1 when the detection criteria have been met (e.g., threshold and duration satisfied), and a value of 0 prior to the detection criteria being met and/or after the termination criteria have been met (e.g., termination threshold and duration satisfied), according to various embodiments of the invention.

Figure 12:
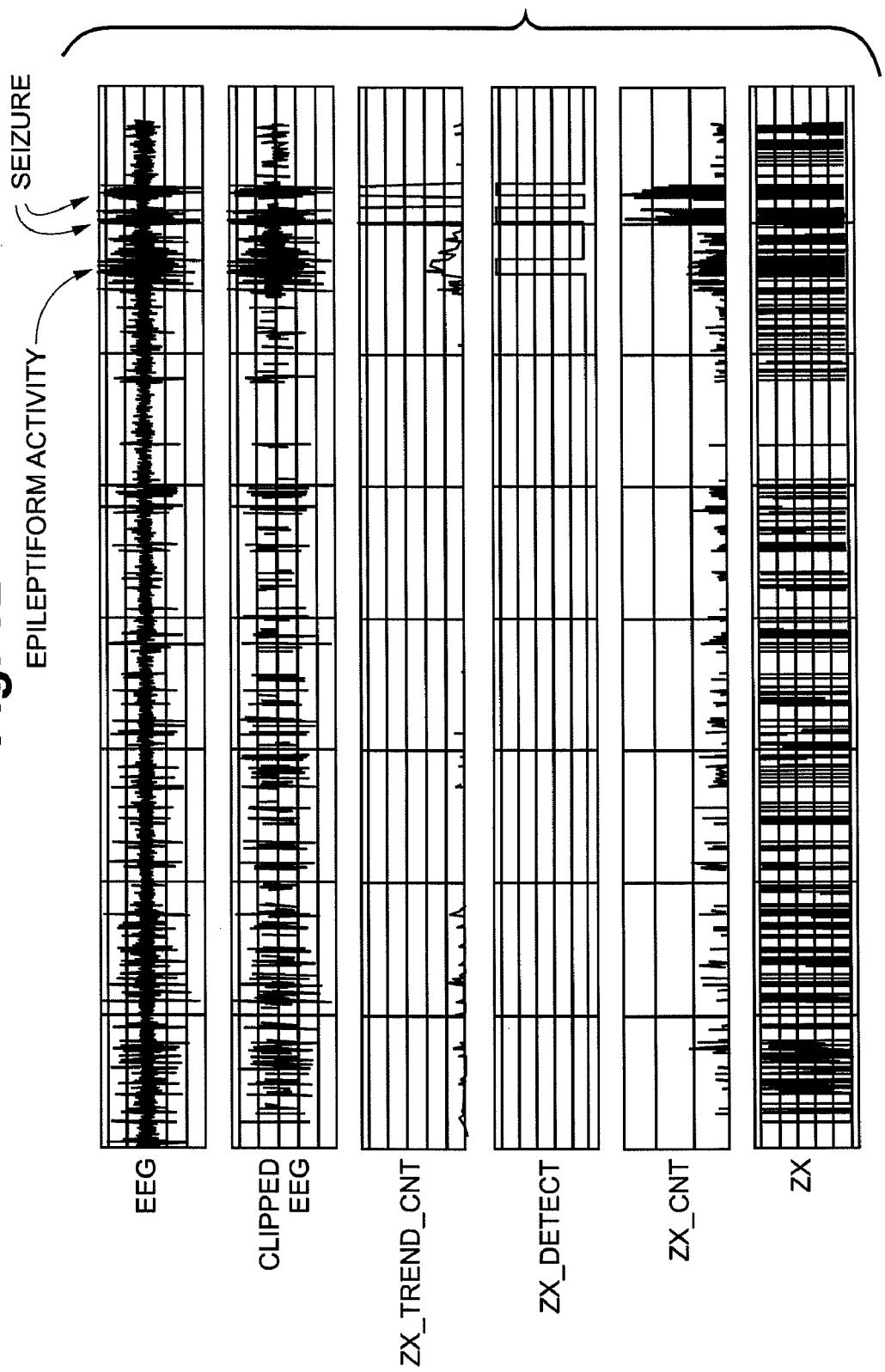
FIG. 12 is a series of plots corresponding to parameters determined by the method of FIG. 10.

FIG. 12 shows an example of the use of the level crossing technique applied to sample EEG signal data that includes seizure activity preceded by epileptiform activity.

Figure 13:
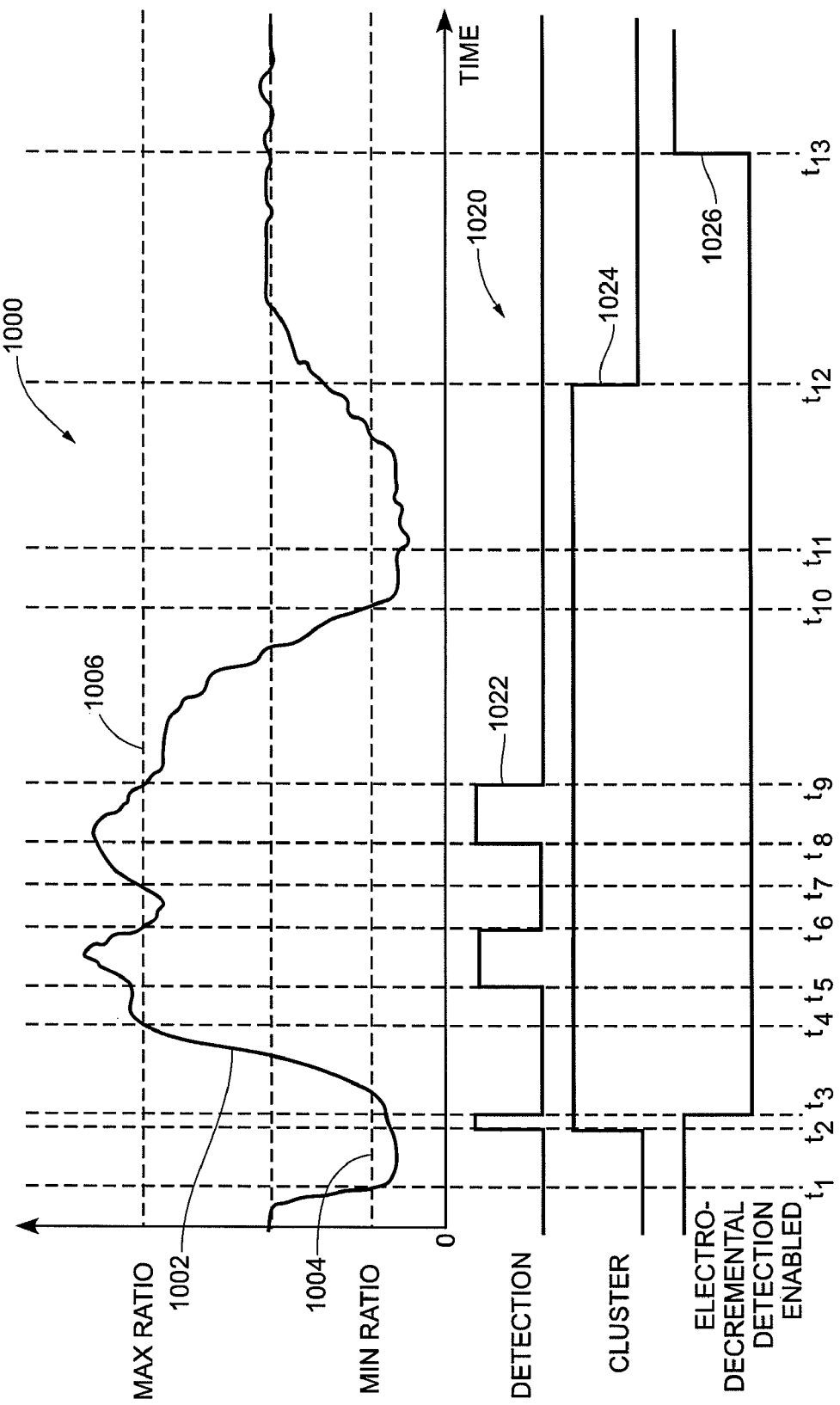
FIG. 13 is a timeline showing a plot of an event monitoring parameter before, during, and after a neurological event.

As shown in FIG. 13, the ZX_DETECT parameter is shown going from a logical value of 0 to a logical value of 1 at three points in time corresponding to epileptiform activity and to subsequent seizure events. Thus, the ZX_DETECT parameter provides the ability to identify a precursor to (e.g., to anticipate) a neurological event such as a seizure, according to certain embodiments of the invention.

IV. Seizure Precursor Detection—Electrodecremental Method

As noted above, seizure activity may be detected by detecting an increase in recent, short-term EEG signal energy levels as compared to longer term (e.g., background) levels, as explained with respect to the ratio seizure detection method discussed above. It has been observed that, in certain cases, a neurological event may also be preceded by decreases in EEG signal energy levels, followed by increases. A method in accordance with certain embodiments of the invention may identify a seizure precursor to a neurological event due to such decreases in EEG signal energy, referred to herein as an electrodecremental detection method. An electrodecremental detection method may provide for an additional or alternate method of identifying a seizure precursor, which may lead to earlier seizure detection and thus, to potentially more effective therapy.

The ratio parameter described above with respect to a ratio detection method may be used to detect a decrease in EEG signal level. (Other event monitoring parameters that compare relatively recent EEG signal levels to longer-term measures of EEG signal levels may also be used, such as the evidence counter method described above.) FIG. 13 shows a time plot 1000 of a ratio 1002 which drops below a minimum ratio threshold, $R_{min}$ 1004 prior to increasing as a result of seizure activity. In certain embodiments, a minimum ratio duration parameter may also be defined, which must be satisfied to detect a seizure precursor, when used. These parameters may be programmable and adjustable, and may thereby be tuned to reduce the number of false positives that may occur. In certain embodiments, nominal values for $R_{min}$ 1004 may correspond to a ratio value of less than about 0.5, and preferably less than about 0.1. In certain preferred embodiments, an $R_{min}$ 1004 value of approximately 0.08 may be used. Similarly, a duration parameter associated with $R_{min}$ 1004 may be selected to an appropriate value based on an amount of time or a specified number of sample intervals, for example.

In certain embodiments, a lock-out period may be employed at startup (e.g., when the algorithm is first employed, or after a device reset, or following a previous detected event) to prevent false detections from the electrodecremental method. For example, if the background energy is initialized to a high value, the ratio parameter may tend to have relatively low values initially, and a false seizure precursor detection may occur based on the ratio being below $R_{min}$ 1004. Thus, a lock-out period may be employed at startup, and may be defined as a predetermined time interval, such as 10 minutes, during which precursor detection based on a ratio parameter falling below $R_{min}$ 1004 may be disabled. The lock-out period may similarly be defined to require at least a minimum amount of EEG signal data to be acquired, for example at startup and/or following certain events, before identifying a neurological event precursor based on the electrodecremental method.

A lock-out period for the electrodecremental detection method may similarly be employed after seizure detection, and/or following the termination of a neurological event, which may include the duration of a seizure and/or the duration of a cluster of related seizure events, for example. [As noted above, U.S. Patent Application Publication 2004/0138536 to Frei et al. ("Clustering of Neurological Activity to Determine Length of a Neurological Event"), which is incorporated by reference herein, discloses a method of detecting a cluster or clusters of neurological events.] This may reduce false detections based upon detection of a post-ictal electrodecremental response, which may occur in some cases due to "post-ictal quieting" following a seizure episode or cluster. In some embodiments, the lock-out period may extend for a certain predefined period beyond the duration of a seizure cluster, for example, with a lock-out period extending approximately 2 minutes beyond the cluster duration in one particularly preferred embodiment. Of course, occurrences other than the end of a cluster timer may also be adapted to trigger the electrodecremental lockout period. Examples of such occurrences include, but are not limited to, the following: the event monitoring parameter dropping below a detection threshold, the end of a period of therapy delivery, or the event monitoring parameter dropping below a lower threshold level following a detected neurological event, for example.

With continued reference to FIG. 13, note that a single event monitoring parameter (e.g., ratio 1002) is plotted with respect to a minimum threshold, $R_{min}$ 1004, as well as to a maximum detection threshold, $R_{max}$ 1006. Of course, a different event monitoring parameter, or multiple event monitoring parameters in combination (e.g., using a MIN function), could be used in conjunction with the threshold $R_{min}$ 1004 for the electrodecremental method than that which is used with the detection threshold $R_{max}$ 1006 for the ratio method, according to various embodiments of the invention; a single parameter is used in FIG. 13 to facilitate the explanation.

The timeline 1000 of FIG. 13 shows several events of interest regarding the use of the electrodecremental detection method, as reflected in the logic states 1020 shown beneath timeline 1000. At time $t_1$, for example, the event monitoring parameter drops below threshold $R_{min}$ 1004. At time $t_2$, a duration parameter associated with $R_{min}$ 1004 has been satisfied, which results in the detection state 1022 going from a logical 0 to a logical 1. The cluster state 1024 also goes from 0 to 1 at time $t_2$, and a cluster timer begins. In certain embodiments, stimulation therapy may begin to be delivered at time $t_2$ as well. In certain other embodiments, charging of stimulation circuitry may commence at time $t_2$ in anticipation of a neurological event. At time $t_3$, the electrodecremental detection method 1026 is disabled, in this example, shortly after detection. Also, since this method is a seizure precursor detection method, no attempt is made to detect a termination of the electrodecremental detection. The detection state 1022 returns to 0 as a result, however the cluster state 1024 remains 1.

At time $t_4$, parameter 1002 exceeds the max ratio threshold, $R_{max}$ 1006 corresponding to the above-described ratio detection method. At time $t_5$, a duration parameter associated with $R_{max}$ 1006 is met and the detection state is again set to 1, and the cluster timer is reset. At time $t_6$, parameter 1002 drops below the max ratio threshold, $R_{max}$ 1006. In the particular example shown, a termination duration of 0 is used, so the detection state 1022 immediately returns to 0. At times $t_7$, $t_8$, and $t_9$, the same process of detection and termination as that described for times $t_4$, $t_5$, and $t_6$ occurs. At times $t_{10}$, and $t_{11}$, the event monitoring parameter 1002 drops below $R_{min}$ 1004, and the duration parameter is satisfied, but no electrodecremental precursor detection occurs here, since the electrodecremental detection method has been disabled to prevent a false detection during a period of post-ictal quieting, such as that shown following time $t_9$ in FIG. 13.

At time $t_{12}$, the cluster timer times out (since there have been no further detections since time $t_9$), and the cluster state returns to a value of 0. The cluster time-out interval in this example corresponds to the period from $t_9$ to $t_{12}$. As shown, the electrodecremental detection method remains disabled (or "locked out") for a period following the end of the cluster corresponding to the time period from $t_{12}$ to $t_{13}$. At time $t_{13}$, the post-cluster lock-out period expires, and the electrodecremental detection method is again enabled.

As noted above, other event monitoring parameters may be used in conjunction with an electrodecremental method of detecting a seizure precursor. For example, the evidence count method may be modified to allow detection of a seizure precursor in accordance with the electrodecremental method. In one possible embodiment, rather than determining whether incoming data magnitude values exceed some multiple of the long-term average (LTA), a multiple of the data magnitude values could be compared to the LTA to determine whether they are below the LTA. For example, if each incoming data magnitude value is multiplied by scale multiple (e.g., a factor of 10), then compared to a magnitude threshold (e.g, the LTA), a stream of comparator output values could be generated whereby a logical 1 could indicate that the value is below the magnitude threshold. The remainder of the evidence count algorithm would operate substantially as described above and would allow for the detection of a seizure precursor in accordance with the electrodecremental method.

Other variations and modifications may become apparent to one of ordinary skill in the art with the benefit of these teachings and would be deemed to fall within the scope of the invention as claimed.

V. Seizure Precursor Detection—Neuro-Cardiovascular Signal Analysis

It has been observed that certain types of information, when used in conjunction with EEG signal analysis, may be useful in improving the specificity with which seizures may be anticipated. For example, analysis of cardiovascular (CV) signals, including electrocardiogram (ECG) and hemodynamic signals (e.g., blood pressure signals), may be performed in conjunction with EEG signal analysis to predict or anticipate seizures according to certain embodiments of the invention.

A method of predicting a seizure event may involve acquiring EEG and CV signals, extracting certain "features" from the EEG and CV signals, and using the extracted features to derive a discriminant measure. The discriminant measure may, for example, be a weighted sum of the extracted EEG and CV features. The discriminant measure may then be compared to a predetermined threshold to predict a seizure event.

The features extracted from the EEG and cardiovascular signals may optionally be compared to a similarity measure to determine how similar the extracted features are to those obtained from the same patient (or from a representative or similar patient) prior to or during an actual observed seizure event, according to certain embodiments of the invention. Likewise, the features extracted from the EEG and cardiovascular signals may also be compared to a dissimilarity measure to determine how dissimilar the extracted features are to those obtained from the same (or a similar) patient prior to or during periods of normal or baseline activity, according to certain embodiments of the invention. The similarity and dissimilarity measures may also be updated to incorporate new information in some embodiments.

Figure 14:
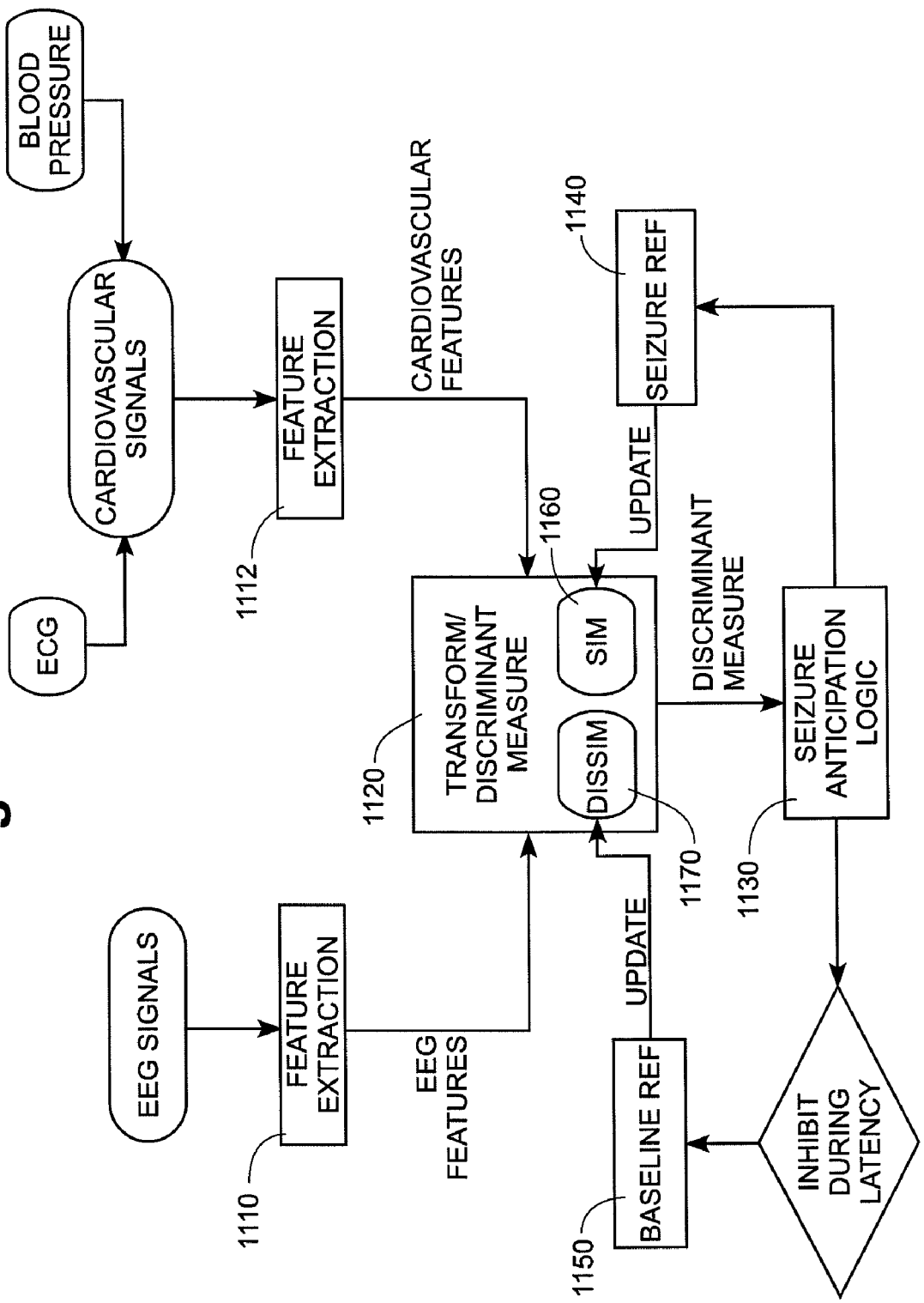
FIG. 14 is a block diagram showing a method of detecting a neurological event using EEG and/or cardiovascular signals according to an embodiment of the invention.

FIG. 14 shows a block diagram of a method of predicting seizure events using both EEG signals and cardiovascular (CV) signals. EEG and CV signals may be acquired in any manner known in the art. In certain embodiments, a feature extraction process may be applied to both signals, which may include a signal transformation or characterization resulting in an output signal. For example, process step 1110 in FIG. 14 may receive one or more acquired EEG signals as an input, and may extract certain "features" from the EEG signals that describe the EEG signals in terms of quantitative values, for example. The feature extraction process of step 1110 may include the determination of one or more of the various event monitoring parameters described above (including any intermediate parameters determined), such as a foreground signal (FG), a background signal (BG), a ratio of FG and BG, a long-term average (LTA), evidence counts, level crossing counts, and level crossing trend counts, for example without limitation. Other features or sets of features may be determined and used as well.

An example of extracting EEG features may include the use of a "zero-crossing" technique. A zero-crossing technique may use the timing of EEG signal polarity changes to derive EEG features. For example, the time intervals between zero crossings (e.g., between signal polarity changes) may be determined, and a measure of the time intervals (e.g., a statistical representation) over a given time frame may be computed to produce one or more of the EEG features. In certain embodiments, zero crossings in the same direction may be employed as the basis for determining the time intervals. For example, the time intervals between transitions in signal polarity from negative to positive values (or vice versa) may be used. In some embodiments, the statistical representation of the time intervals may be computed as the mean value and/or standard deviation of the time intervals over a given time frame, or for a number of periodic time frames (e.g., successive time frames), for example.

In certain embodiments, the statistical representation of the time intervals may be computed for a number of different frequency bands, for example, by applying the EEG signal to one or more passband filters prior to determining the time intervals and statistical representations. Passband filters corresponding to physiological frequency sub-bands may be employed, according to some embodiments of the invention. Such physiologic frequency sub-bands may encompass a range of frequencies from 0-50 Hz, and may include sub-bands at 1-4 Hz, 4-8 Hz, 8-12 Hz, and 12-40 Hz, according to some embodiments of the invention. Of course, the particular frequency bands and sub-bands chosen may vary from these and/or may be adapted for particular patients, according to certain embodiments of the invention.

In other embodiments, the extracted features (such as the statistical information regarding the timing of zero crossings, described above) from a number of different EEG signal channels may be compared to each other to compute a measure of synchronization, for example, using cross-correlation or other suitable measures. A measure of synchronization may also be computed for the features extracted from two or more frequency sub-bands, according to certain embodiments.

With continued reference to FIG. 14, process step 1112 may receive one or more cardiovascular (CV) signals as inputs, including ECG and hemodynamic signals. Step 1112 may entail one or more different types of feature extraction from the CV signals, including assessments of changes in heart rate (e.g., heart rate trend information), cardiac hyper-excitability (or marginality), and autonomic nervous system (ANS) modulation, for example. Feature extraction in step 1112 typically involves characterizing physiologic signals, such as ECG signals and blood pressure signals, in terms of parameters that can be measured and analyzed. Features that may be extracted from an ECG signal may include, but are not limited to, heart rate, as determined by R-R intervals (i.e., the intervals between intrinsic ventricular depolarizations), Q-T intervals, measures of heart rate variability (non-parametric and parametric), and rates of increase or decrease in heart rate. Other features that may be extracted from cardiovascular signals may include measures of blood pressure (e.g., systolic and diastolic) and flow, for example. In certain embodiments, a multi-dimensional analysis of heart rate and blood pressure may be used to derive an indicator (or indicators) of autonomic nervous system (ANS) modulation (by using techniques such as blind source separation, for example). A technique for deriving an index of ANS modulation using blind source separation is provided in U.S. Published Patent Application 2004/0215263. Several feature extraction methods are described below in more detail.

The outputs of steps 1110 and 1112 are the values of the features extracted from both the EEG and cardiovascular signals, respectively. The features are then input to a discriminator 1120, which produces a discriminant measure signal (e.g., an event monitoring parameter), which may be applied to seizure anticipation logic 1130. For example, the EEG features from step 1110 may be combined with the cardiovascular features from step 1112 according to combinational logic in the discriminator 1120 to derive a discriminant measure, which may improve the specificity of seizure anticipation logic 1130. Combinational logic may, for example, comprise weighting the various features extracted according to reliability or importance, and forming a weighted sum of the features to produce a discriminant measure (or event monitoring parameter) for input to seizure anticipation logic 1130.

Seizure anticipation logic 1130 may analyze the incoming discriminant measure to make a decision regarding prediction of a seizure event. (A decision to "predict" or "anticipate" a seizure event may be made prior to a seizure actually occurring, and merely indicates that a seizure is likely to occur; an actual seizure event may not necessarily follow a prediction decision. Thus, the terms "prediction" and "anticipation" have been used here rather than "detection" to distinguish from methods which detect the actual occurrence of a seizure.) A threshold level and an optional duration parameter may be included as part of seizure anticipation logic 1130. For example, a seizure event may be predicted when the discriminant measure exceeds a predetermined threshold for a predetermined duration, according to certain embodiments.

In certain embodiments of the invention, the ability to predict a seizure event in a particular patient may be improved by including a "similarity" measure 1160 as part of the discriminator 1120. Similarity measure 1160 may be used to compare the features extracted (from either or both of steps 1110 and 1112) to the features corresponding to a "reference seizure" 1140 (e.g., features representative of seizures in the same patient or a similar patient). A determination may be made of how similar the current extracted features are to those of the reference seizure 1140, which may affect the weighting assigned to various features and/or the calculation of the discriminant measure. Similarly, the ability to predict a seizure may be improved by using a "dissimilarity" measure 1170 (either alone or in conjunction with the similarity measure), which compares the features extracted (from either or both of steps 1110 and 1112) to the features corresponding to a "reference baseline" 1150 (e.g., features representative of periods of normal or baseline activity from the same patient or a similar patient). A determination may be made of how dissimilar the current features are to the baseline reference 1150, which may likewise affect the weighting assigned to various extracted features and/or the calculation of the discriminant measure.

In further embodiments, the similarity and dissimilarity measures 1160, 1170 may be further enhanced by having the ability to provide updates to either or both of the seizure reference 1140 and baseline reference 1150 values. The updates may comprise new seizure reference or baseline reference information obtained for a particular patient, for example. The seizure reference may be updated by replacing the existing seizure reference information with new information from a recent seizure event for a particular patient, in one possible embodiment. In other embodiments, the seizure reference may be updated by adding or incorporating a recent seizure event to the existing seizure reference to form a weighted average, for example. Updates to the baseline reference may be made in manner analogous to that just described for the seizure reference.

Feature extraction of cardiovascular signals may be based on changes (e.g., increases) in heart rate in some embodiments. For example, a feature may provide an indication of whether heart rate has increased above a certain rate (e.g., tachycardia) in certain embodiments. In other embodiments, a feature may indicate whether the heart rate has increased (or decreased) suddenly, for example, by greater than X beats per minute within a predefined time period.

Feature extraction of cardiovascular signals may also be based on cardiac hyper-excitability (or marginality) in some embodiments. (Marginality reflects the presence and/or amount of non-coordinated chronotropic responses.) For example, an extracted feature describing the marginality of a cardiovascular signal may include statistical information about R-R intervals over predetermined time intervals (e.g., every six minutes). An extracted feature describing the marginality of a cardiovascular signal may also indicate the number of ectopic and marginal events over a given time interval, for example.

Another method of feature extraction of cardiovascular signals may be based on autonomic nervous system (ANS) activity or modulation in certain embodiments. A method of determining an indicator (or index) of ANS modulation is disclosed in commonly assigned U.S. patent application Ser. No. 10/422,069, relevant portions of which are incorporated by reference herein. In certain embodiments, R-R intervals and blood pressure measurements may be used to derive an index of ANS modulation using multi-dimensional analysis, for example, using a technique such as blind source separation. If only R-R intervals are available, for example, classical heart rate variability analysis can be used (parametric or non-parametric).

Signal Quality—Clip Count Algorithm

In the seizure detection methods described above, the input signals were assumed to be of good quality. However, certain situations or problems may arise that cause an input signal to "flat line," saturate, stick to one rail or the other, bounce between rails, or otherwise deteriorate in quality. For example, a fractured or dislodged lead may cause the input signal to "rail" high or low. Since the above described seizure detection methods rely on the quality of the input signals to possibly form the basis for episode storage and/or therapy delivery or other decision-making processes, it would be desirable to provide a method of disabling detection methods in the presence of such problematic input signals, and subsequently re-enabling detection methods once such signals are no longer present.

In an embodiment of the invention, a method is described for detecting "clipping" of input signals that may affect a seizure detection algorithm, such as those described above. In certain embodiments of the invention, an IMD may be adapted to perform a method which analyzes input signals to detect clipping of the input signals, and which may further disable or enable processing of a seizure detection algorithm in response to such analysis. Although embodiments of the invention will be described below in the context of an implantable seizure detection algorithm, one of ordinary skill in the art with the benefit of these teachings will recognize that the methods and devices described herein may be used in other signal sensing and processing applications.

One way of defining whether a signal has been "clipped" is by determining when the difference in amplitude between consecutive input data points is less than or equal to some predefined parameter, for example, according to certain embodiments. The predefined parameter, or "clipping tolerance," Ct, may be defined using the following logic:

If $|x_n - x_{n-1}| \leq C_t$, then data point $x_n$ may be said to be "clipped,"

where $x_n$ and $x_{n-1}$ are the signal values of consecutive data points. The clipping tolerance, $C_t$, may be set to a value of zero in certain embodiments, thereby requiring that $x_n$ and $x_{n-1}$ be equal to each other to indicate clipping. In other embodiments, it may be desirable to use other (e.g., non-zero) values for $C_t$. A zero value for $C_t$ may be appropriate, for example, in embodiments where the input signals comprise digital data, e.g., binary representations of signal levels. In such an embodiment, the clipping tolerance is effectively equal to the resolution of the least significant bit. In embodiments using non-zero values for clipping tolerance, $C_t$ could be defined in terms of a specified number of bits of signal resolution. For example, if $C_t$ is set to 2 bits, then a data point with a binary signal value of "000 001" following a data point with a binary signal value of "000 011" would be identified as a clipped data point, since it has an amplitude that is within 2 bits of signal resolution from the amplitude of the preceding data point.

A method in accordance with an embodiment of the invention may attempt to determine whether a relatively high percentage of recent data points are clipped, indicating that there may be a problem with signal quality. In one embodiment, a running measure of clipped signals, referred to herein as the "clip count," or $C_c$, may be obtained by evaluating successive data points against the clipping tolerance, $C_t$, and either incrementing or decrementing the clip count based on the result as follows:

If $|x_n - x_{n-1}| \leq C_t$, then $C_c = C_c + 1$, else $C_c = C_c - 1$.

In certain embodiments, clip count $C_c$ may be initialized to a value of 1, for example. In certain further embodiments, clip count $C_c$ may be based upon an evaluation of a rolling window or buffer of a predetermined number of sample points (or equivalently, a number of sample points acquired over a defined first period), and may be determined as a weighted average, or other appropriate measure of signal data. In some embodiments, the clip count parameter, $C_c$, may be determined as a running measure (e.g., an unbounded first period), as described by the above equation, but may be bounded by a maximum value, $C_{max}$, and/or a minimum value, $C_{min}$ (e.g., a ceiling and a floor value, respectively). For example, If $C_c > C_{max}$, then $C_c = C_{max}$, and if $C_c < C_{min}$, then $C_c = C_{min}$.

In order to use the clip count, $C_c$, to control the input signal quality for a seizure detection algorithm, a saturation threshold value, $T_d$, and a non-saturation threshold, $T_e$, may be defined to determine when to disable seizure detection and/or precursor detection signal processing, as well as when to re-enable signal processing, respectively. In certain embodiments, the threshold values may be incorporated into decision-making logic as follows:

If $C_c \geq T_d$, disable processing of a seizure detection algorithm, and if $C_c \leq T_e$, re-enable processing of a seizure detection algorithm.

In certain further embodiments of the invention, a duration parameter may also be defined such that $C_c$ must exceed threshold $T_d$ for a predetermined period of time (e.g., duration $D_d$) before seizure detection processing is disabled, and $C_c$ must drop below threshold $T_e$ for a predetermined period of time (e.g., duration $D_e$) before seizure detection processing is re-enabled.

It should be noted that "disabling" signal processing, as described above, may comprise suspending data input, or suspending the processing of data by a seizure detection algorithm, or suspending any output generated by a seizure detection algorithm, or some similar actions or combinations of actions. Similarly, "enabling" signal processing (e.g., when a signal saturation condition terminates) may typically involve reversing the actions taken to disable signal processing, but may include alternate or additional steps as well.

Figure 15:
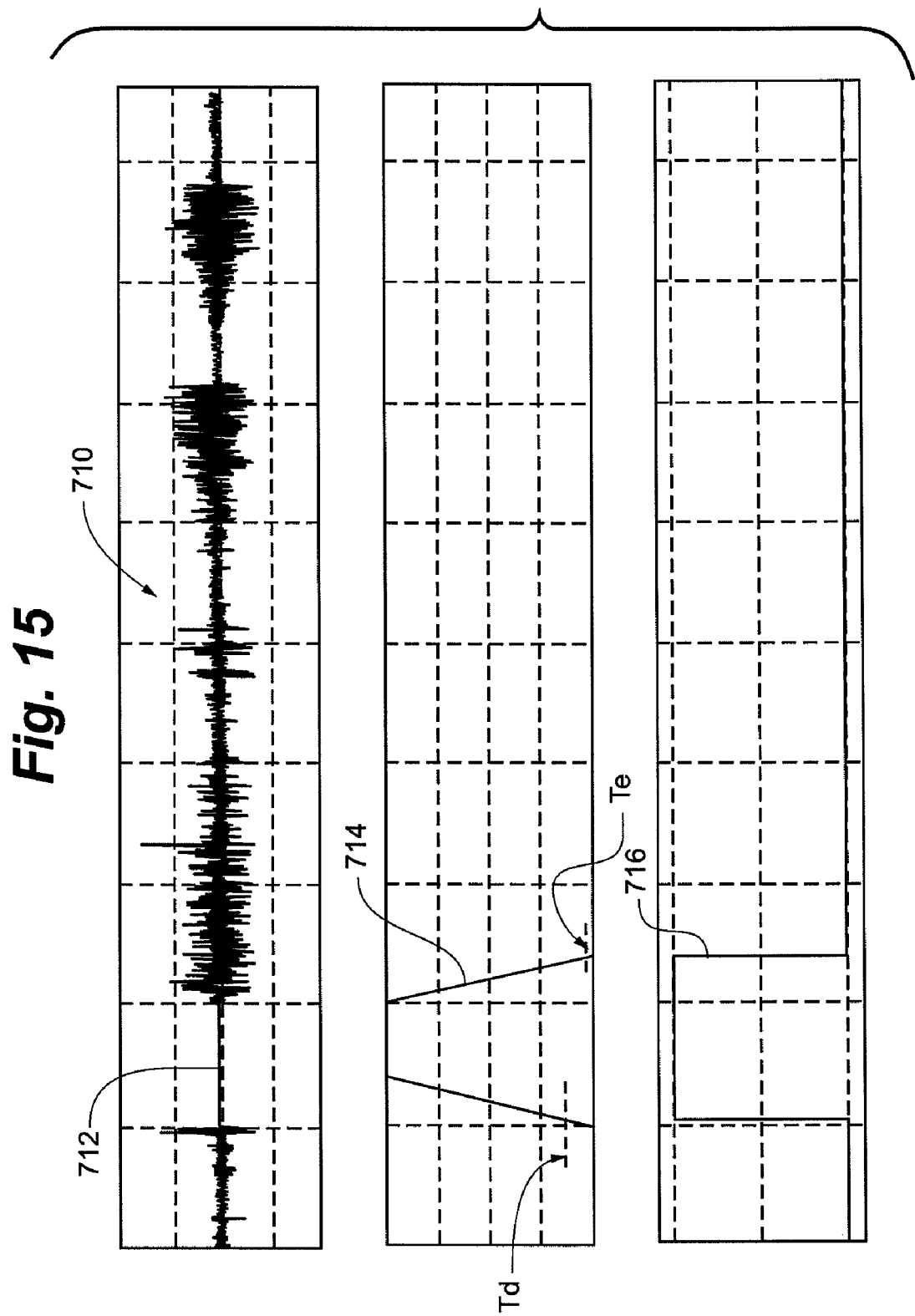
FIGS. 15 through 17 are a series of time plots illustrating a method of identifying signal saturation according to an embodiment of the invention.

FIG. 15 shows an example of the above-described clip count algorithm being used to evaluate signal quality during analysis of an EEG signal. Raw EEG signal 710 is shown in the upper pane of FIG. 15, signal 710 having a flat line or saturated portion, as indicated at 712. The clip count $C_c$ signal 714 is shown in the middle pane of FIG. 15, and a disable function 716 is shown in the lower pane of FIG. 15. In the particular example shown, a floor value for clip count $C_c$ is set at $C_{min}=1$, a ceiling value for clip count $C_c$ is set at $C_{max}=4000$, a threshold $T_d$ for disabling the seizure detection algorithm is set at $T_d=500$, and the threshold $T_e$ for re-enabling the seizure detection algorithm is set at $T_e=50$.

As shown in FIG. 15, as EEG signal 710 saturates at 712, clip count $C_c$ signal 714 begins to increase due to the incrementing of $C_c$ described above. When clip count $C_c$ signal 714 reaches a value of 500 (corresponding to threshold $T_d$), the disable function 716 becomes true, corresponding to a change in logical value from 0 to 1 as shown. When the saturated portion 712 ends, clip count $C_c$ signal 714 begins to decrease linearly due to the decrementing of $C_c$ described above. When clip count $C_c$ signal 714 drops to a value of 50 (corresponding to threshold $T_e$), the disable function 716 becomes false, corresponding to a change in logical value from 1 to 0 as shown.

Figure 16:
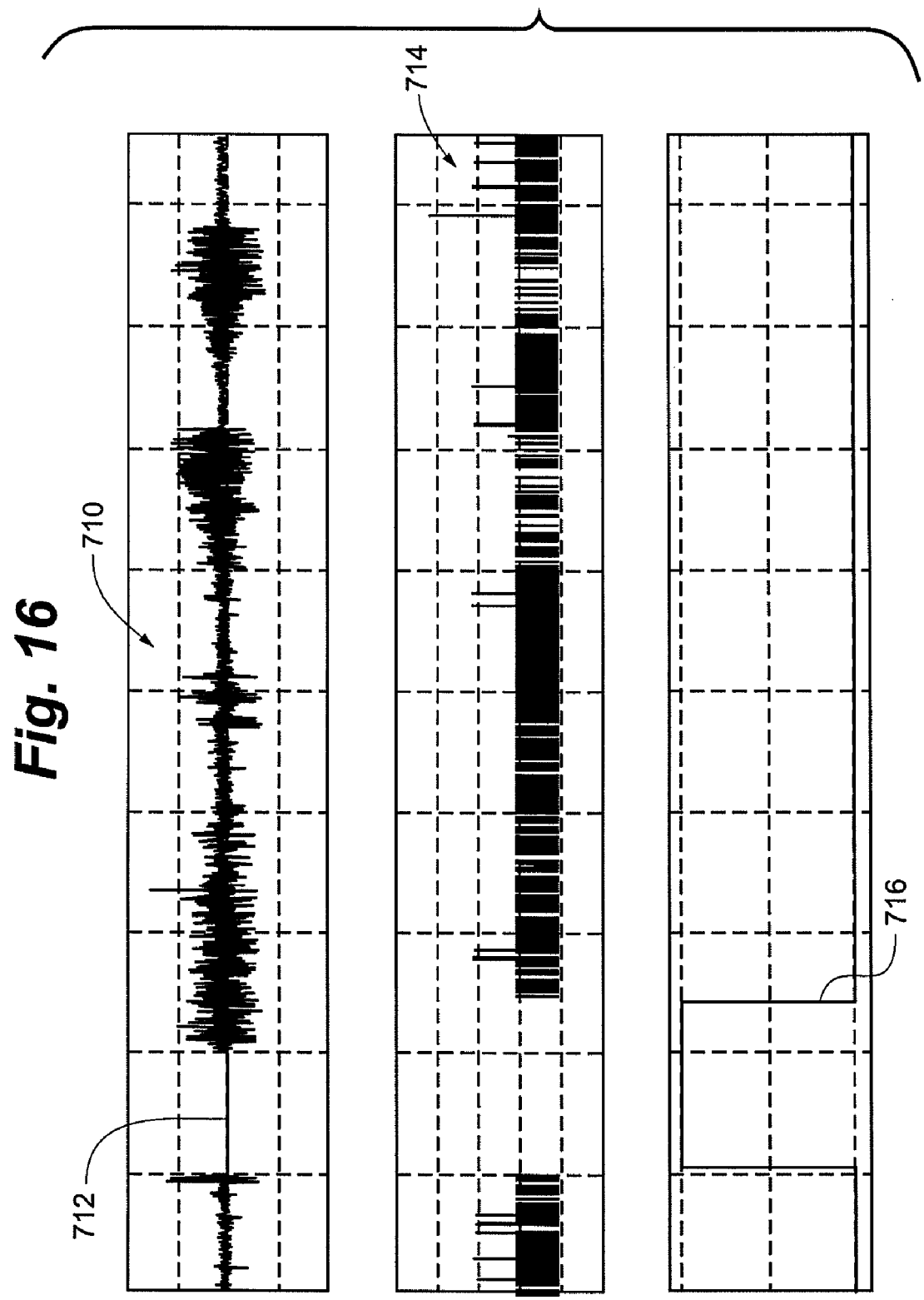

FIG. 16 shows the same signals 710, 714, and 716 shown in FIG. 15, but includes a greatly enlarged view of signal 714 wherein the vertical axis for the clip count only extends from a value of 0 to 5. This view illustrates the robustness of the clip count algorithm by revealing that the clip count $C_c$ signal 714 tends to remain at a relatively low level (e.g., between 1 and 5) when processing valid physiologic signals (e.g., without saturation of the amplifiers and/or analog-to-digital converters). Note, for example, that the clip count $C_c$ signal 714 does not exceed a value of 4 in the entire frame shown with the exception of the portion corresponding to the flat-lined portion 712. Thus, the clip count $C_c$ signal 714 does not even approach the threshold value ($T_d=500$) for disabling a seizure detection algorithm in the example shown in any portion other than flat-lined portion 712.

Figure 17:
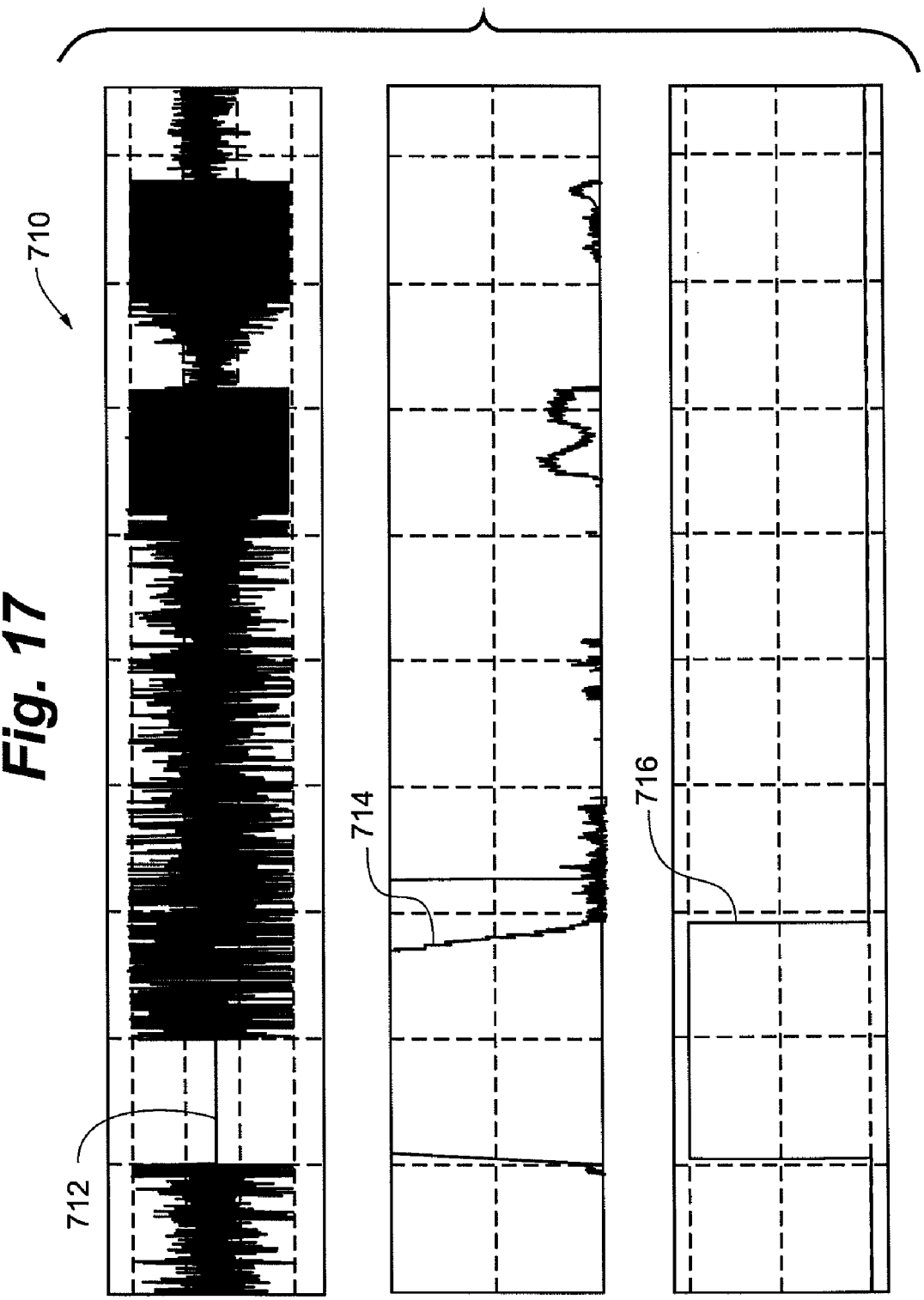

FIG. 17 again shows signal 710 from FIGS. 15 and 16, but includes a situation where clipping of signal 710 has been imposed by clipping the signal 710 within a range of values between 1900 and 2200 as shown. Despite what appears to be a significant amount of clipping throughout the raw EEG signal, the clip count $C_c$ tends to remain relatively low for all portions of the signal other than the actual flat-lined portion 712, and does not again exceed the threshold $T_d$ after returning below the threshold $T_e$ following the flat line portion 712. This situation might occur, for example, if the gain is set too high for the amplifier or A/D converter. As shown, the clip count algorithm is able to distinguish between a truly saturated signal (e.g., flat-lined portion 712 and) apparent clipping in other portions of the EEG signal 710 which may be caused by device settings, for example.

Figure 18:
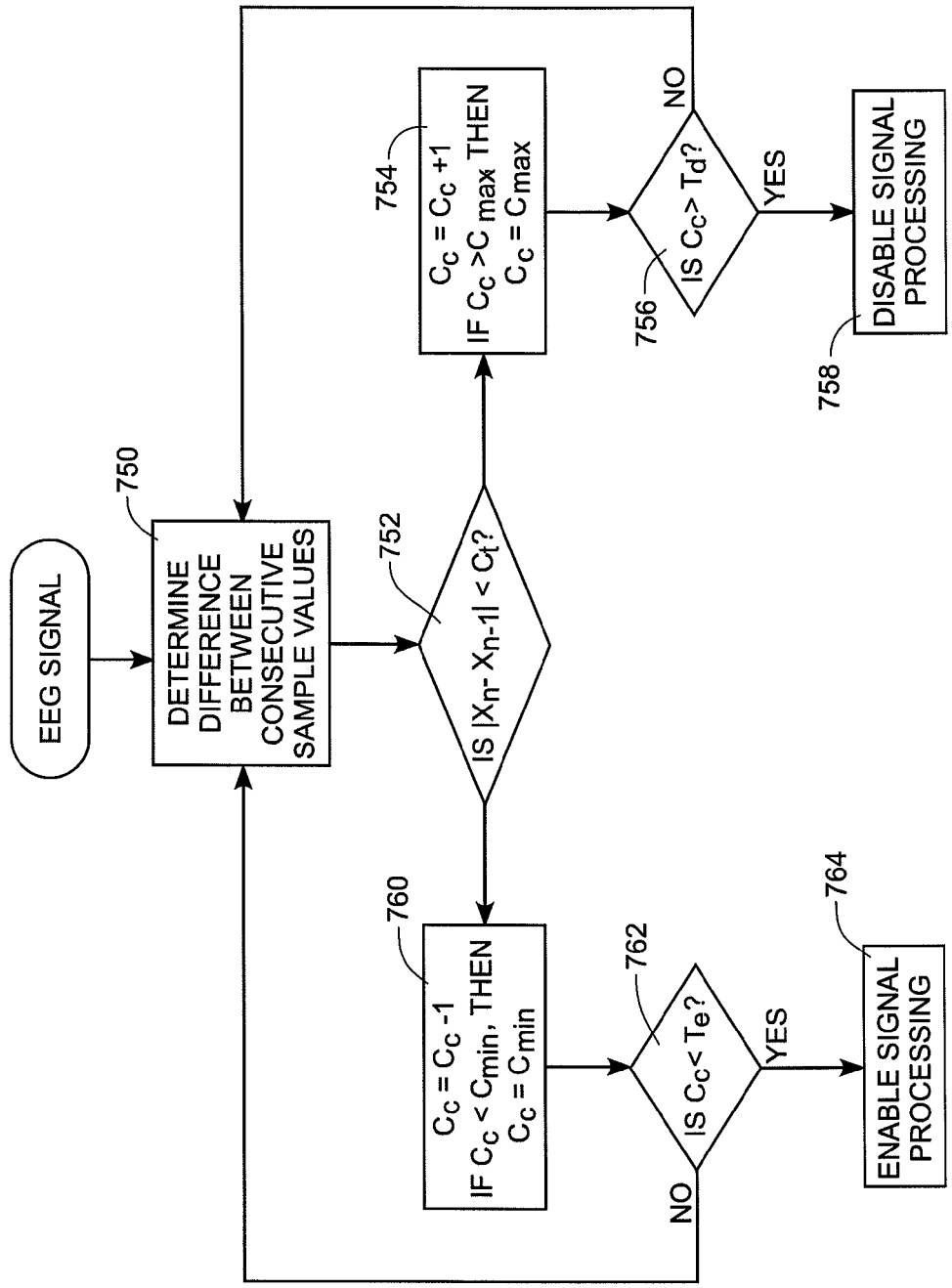
FIG. 18 is a flow chart showing a method of ensuring signal quality in a signal processing system according to an embodiment of the invention.

FIG. 18 is a flow chart of a method of ensuring signal quality by identifying poor signal conditions, due to such problems as clipping and signal saturation, for example. Step 750 involves determining the difference in amplitude between consecutive EEG signal data samples. At step 752, the magnitude of the difference between consecutive data sample values is compared to a clipping tolerance. If the magnitude of the difference between a given data sample and the preceding data sample is less than the clipping tolerance, then step 754 is applied to increment the value of the clip counter, $C_c$. Optionally, as shown in step 754, a ceiling value, $C_{max}$ may be employed to put a limit on how large the clip counter may become. The clip counter value determined at step 754 is then compared to a disable threshold, $T_d$, as shown as step 756. If the clip counter value exceeds the disable threshold, then signal processing may be disabled, as shown as step 758. On the other hand, if the clip counter value does not exceed the disable threshold, then the process returns to step 750 to continue analyzing incoming EEG sample values. If, at step 752, the magnitude of the difference in consecutive signal values was found not be less than the clipping tolerance, then step 760 may be employed to decrement the value of the clip counter, as shown. In certain embodiments, an optional floor may be employed such that the clip counter value cannot decrease below a predetermined amount, $C_{min}$. After decrementing at step 760, the value of the clip counter is compared to an enabling threshold, $T_e$, as shown as step 762. If the clip counter value is less than the enable threshold, then signal processing may be re-enabled, as shown as step 764. Otherwise, the process returns to step 750 to continue analyzing EEG signal values.

Post-Stimulation Detection Algorithm (PSDA)

As noted above, a device that uses a seizure detection algorithm in accordance with various embodiments of the invention may be adapted to deliver therapy in response to a detected seizure event. A device or system according to certain embodiments of the invention may include leads adapted to perform both sensing and stimulation functions. During the delivery of stimulation therapy from such leads, a seizure detection algorithm may be at least temporarily disabled, e.g., to protect amplifier circuitry and/or avoid processing meaningless data. This may be accomplished through the use of hardware blanking, where no data is collected, or through the use of software blanking, where data may be collected on channels not being used for stimulation, but where the data is not processed by a seizure detection algorithm. Following therapy delivery, a time delay may be imposed during which stabilization is allowed to occur prior to analyzing signals for the continuing presence of a neurological event. U.S. Patent Application Publication 2004/0152958 to Frei et al. ("Timed Delay for Redelivery of Treatment Therapy for a Medical Device System"), hereby incorporated by reference in its entirety, discloses such a method of using a time delay following therapy delivery for a neurological event.

Upon the completion of stimulation therapy delivery, it may be desirable to quickly determine the need for additional stimulation therapy, since the effectiveness of such therapy may diminish with time. The seizure detection algorithm used to detect the seizure event and trigger stimulation therapy in response thereto may not be ideally suited for rapidly determining the need for additional subsequent stimulation therapy. The foreground signal (FG) described above, for example, may take several seconds following stimulation therapy to resume providing a ratio calculation based on post-stimulation data. Since time delays in delivering therapy are believed to be a factor in determining the success of a therapy, a method is desired that can quickly determine whether a seizure episode is still in progress following the delivery of stimulation therapy and/or assess the need for additional stimulation therapy. Such a method may be used following a stimulation therapy until enough time has elapsed to allow for a return to the "normal" seizure detection algorithm, for example.

Figure 19:
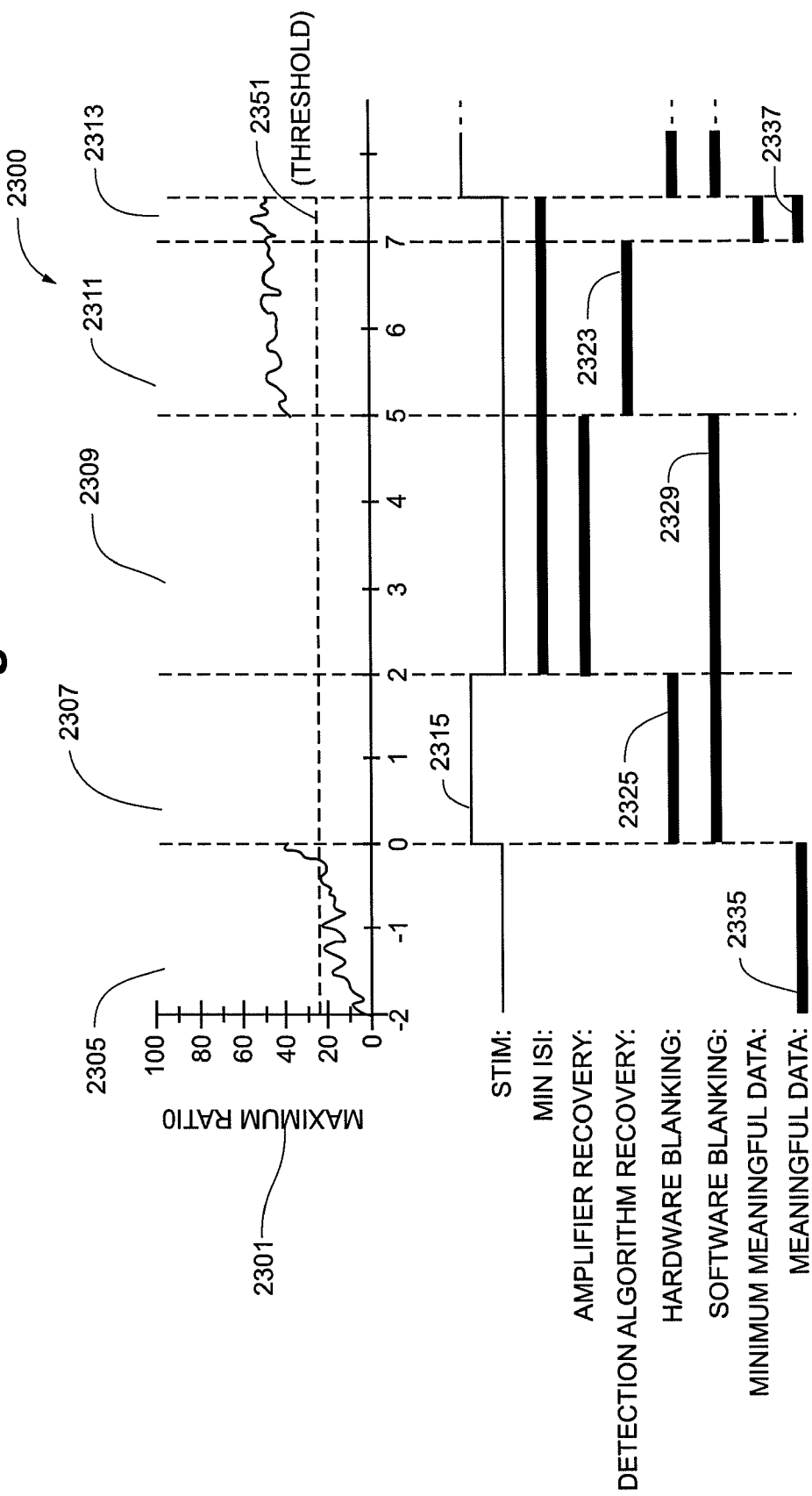
FIG. 19 is a timeline plot illustrating the potential effects of therapy delivery on the ability to detect neurological events.

FIG. 19 shows a timeline drawing that illustrates the above-described situation. FIG. 19 shows a timing diagram for an event monitoring parameter 2301 in accordance with certain embodiments of the invention. Parameter 2301 may, for example, be a ratio of foreground to background EEG signal energy as described above with reference to FIG. 7. The event monitoring parameter 2301 may further comprise a maximal ratio, for example, the largest ratio of a set of ratios (e.g., from multiple EEG signal channels), in which each ratio is determined by a short-term representation of a neurological signal divided by a corresponding long-term representation.

Signal data 2300 comprises signal segments 2305, 2307, 2309, 2311, and 2313. During segment 2305, signal data 2300 is collected, processed, and tracked by the medical device system in order to determine if a seizure is occurring. As a result of the seizure detection at the end of interval 2305 (e.g., based on the seizure detection algorithm's analysis of input signal data 2300 during time interval 2335), the medical device delivers an electrical stimulation pulse 2315 to a desired set of electrodes. Other embodiments of the invention, of course, may use forms of therapeutic treatment other than an electrical stimulation pulse, or in conjunction with an electrical stimulation pulse.

During stimulation pulse 2315, a corresponding channel is blanked by hardware during a hardware blanking interval 2325 so that no signal is collected or analyzed during this interval of time. A software blanking interval 2329 is also shown. During software blanking interval 2329, for example, the medical device system does not process signal data acquired during segments 2307 and 2309. In some embodiments, the medical device system may not collect signal data during software blanking interval 2329, while in other embodiments, the signal data may be acquired but not processed. In certain embodiments, software blanking may occur on a subset of all channels, including channels not being stimulated. Also, the set of channels that employ software blanking may be different from the set of channels that employ hardware blanking. U.S. Patent Application Publication 2004/0133248 to Frei et al. ("Channel-Selective Blanking for a Medical Device System"), hereby incorporated by reference in its entirety, discloses such a method of blanking certain channels during the delivery of therapy from one or more of the channels.

After software blanking interval 2329, the medical device system may resume analyzing signal data 2300 using a seizure detection algorithm during recovery interval 2323 and may produce an output corresponding to segment 2311 in FIG. 19. As noted, a seizure detection algorithm may utilize a relatively short-term representation of EEG signal energy, such as the approximately two-second foreground window, FG, according to certain embodiments of the invention. The algorithm recovery interval 2323 in such an embodiment would therefore be approximately two seconds. Meaningful data 2337 acquired after the algorithm recovery interval 2323 may thereafter be used to determine whether treatment therapy was effective, or whether the seizure is continuing. However, intervals 2323 and/or 2337 may represent periods of time during which additional therapy may be warranted, and during which delays in delivering therapy may reduce the effectiveness of such additional therapy.

A method of detecting a seizure event following delivery of stimulation therapy is described below with reference to FIGS. 19 and 20. FIG. 19 illustrates the operation of a post-stimulation seizure detection algorithm that may be used in conjunction with a "normal" seizure detection algorithm, according to an embodiment of the invention. For example, stimulation therapy 2315 may be delivered by an IMD upon detection of a seizure (beginning of segment 2307) using a "normal" seizure detection algorithm (e.g., by signal 2301 exceeding threshold 2351 for a predetermined duration). The normal seizure detection algorithm may rely on both long-term and short-term EEG signal representations, for example. Following stimulation 2315, a post-stimulation detection period 2311, 2313 may occur, during which a post-stimulation detection algorithm may operate, either alone or in conjunction with the normal seizure detection algorithm. The output of the post-stimulation detection algorithm may be used, for example, to allow for detection (e.g., re-detection) of seizure activity during the post-stimulation detection period 2311, 2313 according to certain embodiments. This may be desired to provide a post-stimulation seizure detection algorithm which can assess the need for additional stimulation therapy, and trigger such therapy, until at least the short-term component of the normal seizure detection algorithm acquires sufficient post-stimulation data to allow resumption of the normal seizure detection algorithm.

Once the short-term component of the normal seizure detection algorithm has a sufficient amount of post-stimulation data, seizure detection may resume according to the normal seizure detection algorithm, as shown at period 2337 in FIG. 19.

In certain embodiments of the invention, a post-stimulation detection counter, C, may be defined using post-stimulation data. A method of determining and using a post-stimulation detection counter, C, to detect seizure activity following delivery of stimulation therapy is shown in FIG. 20. The method shown may be employed upon delivery of stimulation therapy (or soon thereafter), as indicated at 2440. For example, post-stimulation detection counter, C, may be initialized to an initial value, $C_0$, following delivery of stimulation therapy, as shown at 2442. The initial value, $C_0$, may be set to a value of zero, or may be set to some other value (e.g., 200) according to user preference, for example. A stream of post-stimulation EEG signal data values, $U_n$, is acquired as shown at 2444 and compared to a level cutoff at 2446. The signal data values, $U_n$, may comprise input amplitude data obtained at a sample rate (e.g., 250 samples per second) according to certain embodiments.

If a given $U_n$ value is equal to or exceeds the level cutoff 2446 as determined at step 2448, the post-stimulation detection counter, C, is incremented by a specified increment amount (e.g., $C_n = C_{n-1} + 1$), as shown at step 2450. If instead, a given $U_n$ value is below the level cutoff 2446 as determined at step 2448, the post-stimulation detection counter, C, is decremented by a specified decrement amount (e.g., $C_n = C_{n-1} - 1$), as shown at step 2452. More generally, If $U_n \geq k*BG$, Then $C_n = C_{n-1} + (\text{increment})_{PS}$ Else, $C_n = C_{n-1} - (\text{decrement})_{PS}$, where k*BG represents the value of the level cutoff 2446 (discussed in more detail below), and where $(\text{increment})_{PS}$ and $(\text{decrement})_{PS}$ are the increment and decrement amounts, respectively.

In certain embodiments of the invention, the values of $(\text{increment})_{PS}$ and $(\text{decrement})_{PS}$ may be set to integer values, such as 0, 1 or 2. In certain preferred embodiments, both values may be set to 1.

The value of the post-stimulation detection counter, C, may next be compared to a post-stimulation detection threshold, $PS_{th}$, as shown at 2454, for example, after incrementing C. If the value of C equals or exceeds the post-stimulation detection threshold, $PS_{th}$, a post-stimulation seizure event may be considered "detected," as indicated at 2456. Additional stimulation therapy may be delivered in response to a detected post-stimulation seizure event, as shown at 2458. An optional duration parameter, $PS_{dur}$, could also be defined (in which case, C would need to equal or exceed $PS_{th}$ for the prescribed duration parameter to cause a detection), but $PS_{dur}$ would typically be given a value smaller than the duration value used (if any) during normal seizure detection processing.

In a particular exemplary embodiment, $PS_{th}$ may be set to a value of 100, for example, requiring that counter C reach or exceed a value of 100 to detect a post-stimulation seizure event and/or to deliver subsequent stimulation therapy. If an increment value of 1 is chosen for step 2450, for example, it may be possible for the post-stimulation detection counter C to reach a value of 100 in less than a half-second, assuming a sample rate of 250 samples per second. Of course, these values could be adjusted to meet the needs of a particular patient, or the requirements of a particular physician. Upon completion of any additional stimulation therapy delivery, the post-stimulation detection process may begin once again.

Figure 20:
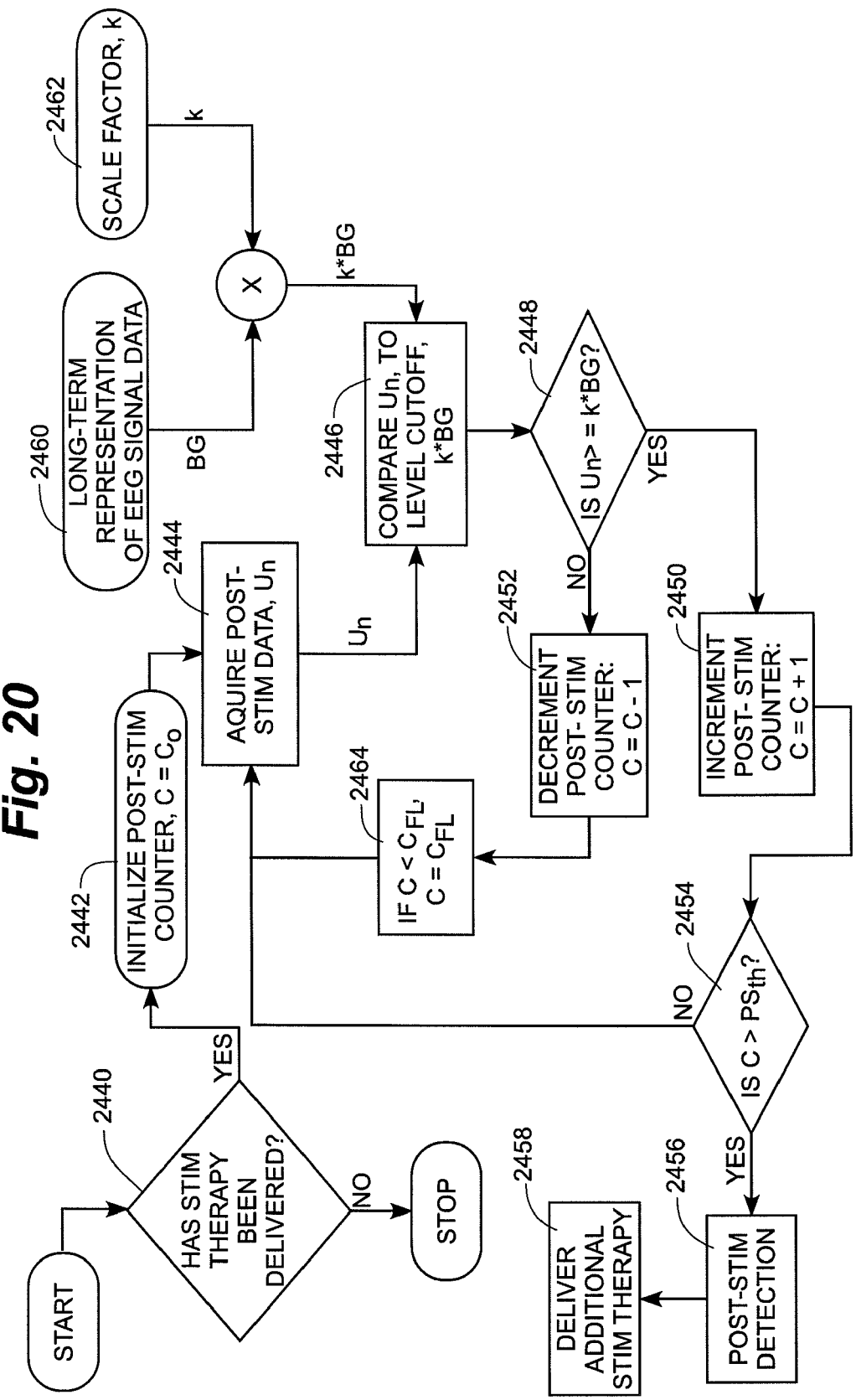
FIG. 20 is a block diagram showing a method of detecting a neurological event following therapy delivery according to an embodiment of the invention.

As shown in FIG. 20, post-stimulation data $U_n$ continues to be acquired and evaluated after incrementing 2450 (or decrementing 2452) the post-stimulation counter, unless a post-stimulation seizure event is identified. FIG. 20 also shows that the level cutoff 2446 used for comparing to the incoming data $U_n$ may be determined from a long-term representation of EEG signal data. In one embodiment, the level cutoff may be a function of a long-term component of the normal seizure detection algorithm. In certain embodiments, a long-term representation of EEG signal data that is at least partially (and in some cases, entirely) based on pre-stimulation EEG signal values may be used to determine the level cutoff 2446. In certain further embodiments, the long-term representation of EEG signal data may be updated to incorporate both pre-stimulation values and newly acquired post-stimulation values. In a preferred embodiment, the long-term representation may comprise a recent value of a background signal, BG, determined prior to stimulation (or perhaps a somewhat earlier value of BG), and updated to include newly acquired post-stimulation data values, wherein BG is determined substantially as described above. In an alternate embodiment, the long-term representation may comprise the last (e.g., most recent) value of a long-term average, LTA, determined prior to stimulation (or perhaps a somewhat earlier value of LTA), and updated to include post-stimulation data values. LTA may be determined using a counter substantially as described above.

In further embodiments, the value 2460 may be multiplied by a scale factor, k, shown at 2462, to obtain the level cutoff 2446. The scale factor k may be adjustable and need not be the same as that used by the detection logic of the normal seizure detection algorithm.

In certain further embodiments, a "floor" value, $C_{FL}$, may be set to limit how low the post-stimulation detection counter, C, may decrement, according to certain embodiments. This is shown at step 2464. For example, if the value of C would fall below $C_{FL}$ as a result of decrementing C, then C is set equal to the floor, $C_{FL}$:

If $C_{n-1} - (\text{decrement})_{PS} \leq C_{FL}$, then $C_n = C_{FL}$.

Figure 21A:
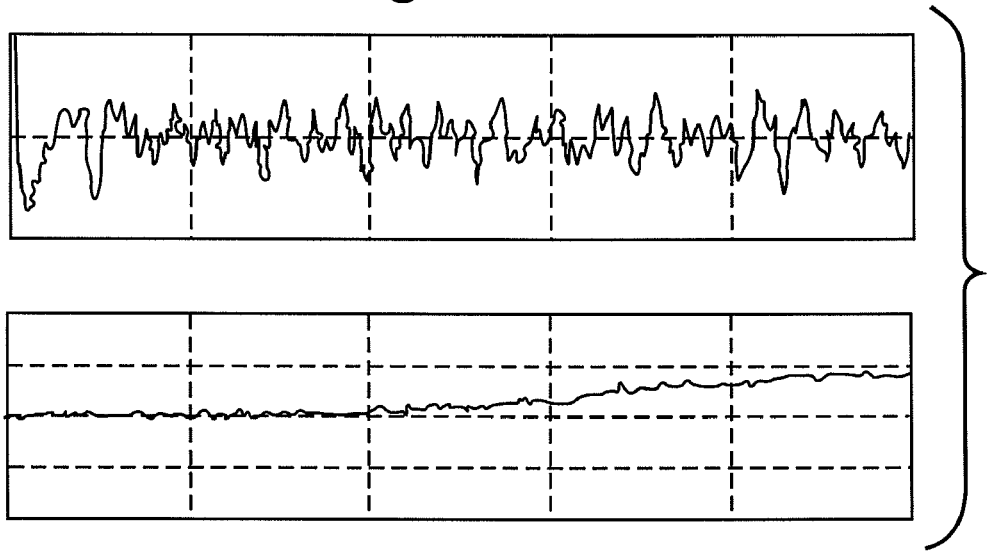
FIGS. 21(a) and 21(b) show time plots of EEG signal data corresponding to simulated post-stimulation neurological events, along with a post-stimulation detection counter according to the method of FIG. 20.
Figure 21B:
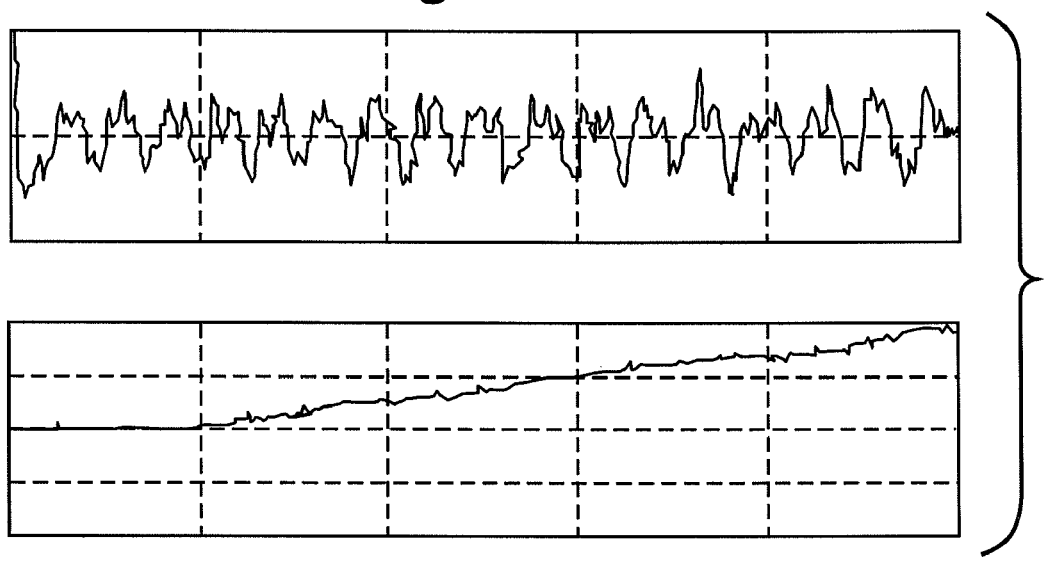

FIGS. 21(a) and 21(b) show time plots of EEG signal data corresponding to simulated post-stimulation seizure events, along with the value of a post-stimulation detection counter, C, derived from the respective EEG signals in accordance with embodiments of the invention. In both examples, the post-stimulation detection counter, C, increases and could be programmed (e.g., by setting the post-stimulation threshold, $PS_{th}$, to an appropriate value) to detect post-stimulation seizure activity (and hence, deliver subsequent therapy) more quickly than by relying on the normal seizure detection algorithm.

Thus, a METHOD AND APPARATUS FOR DETECTION OF EPILEPTIC SEIZURES has been provided. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method of detecting a neurological event, the method comprising:
    acquiring an EEG signal comprising a stream of sampled data values;
    transforming the stream of sampled data values into a stream of data magnitude values;
    determining, with processing circuitry, a long-term representation of the EEG signal from the data magnitude values, comprising comparing a data magnitude value to a previous value of the long-term representation, and incrementing the previous value by a predetermined increment amount if the data magnitude value equals or exceeds the previous value, and decrementing the previous value by a predetermined decrement amount if the data magnitude value is less than the previous value;
    deriving a magnitude threshold from the long-term representation;
    comparing the data magnitude values to the magnitude threshold to produce a stream of comparator output values, each comparator output value indicating whether a given data magnitude value exceeds the magnitude threshold;
    calculating an event monitoring parameter based on a rolling window of comparator output values;
    comparing the event monitoring parameter to an onset threshold; and
    detecting a neurological event when the event monitoring parameter exceeds the onset threshold.

2. The method of claim 1 wherein the neurological event is an epileptic seizure.

3. The method of claim 1 wherein the data magnitude values comprise positive values derived from the stream of sampled data values.

4. The method of claim 1 wherein the data magnitude value that is compared to the previous value of the long-term representation is downsampled from the stream of data magnitude values.

5. The method of claim 1 wherein the previous value of the long-term representation has a predetermined initial value.

6. The method of claim 1 wherein the increment and decrement amounts are the same.

7. The method of claim 1 wherein at least one of the increment and decrement amounts is greater during an initial period after starting the method than following the initial period.

8. The method of claim 1 wherein at least one of the increment and decrement amounts is greater during a post-detection period after termination of an episode than following the post-detection period.

9. The method of claim 1 wherein the long-term representation cannot exceed a predefined maximum value.

10. The method of claim 1 wherein the long-term representation cannot decrease below a predefined minimum value.

11. The method of claim 1 wherein calculating the event monitoring parameter includes counting the comparator output values in the rolling window.

12. The method of claim 1 wherein a neurological event is detected when the event monitoring parameter exceeds the onset threshold for an onset duration.

13. The method of claim 12 wherein a neurological event is detected when a specified number of consecutive values of the event monitoring parameter exceed the onset threshold for an onset duration.

14. The method of claim 12 wherein a neurological event is detected when a predetermined percentage of values of the event monitoring parameter exceed the onset threshold for a detection duration.

15. The method of claim 1 further comprising determining an end of a neurological event when the event monitoring parameter decreases below a termination threshold.

16. The method of claim 15 wherein the end of a neurological event is determined when the event monitoring parameter decreases below a termination threshold for a termination duration.

17. The method of claim 16 wherein the termination duration is complete when a specified number of consecutive values of the event monitoring parameter are below the termination threshold.

18. The method of claim 16 wherein the termination duration is complete when a predetermined percentage of values of the event monitoring parameter are below the termination threshold.

19. The method of claim 15 further comprising holding the long-term representation value constant when a neurological event is detected until the end of the neurological event.

20. The method of claim 15 further comprising assigning a predetermined initial value to the long-term representation at the end of a neurological event.

21. The method of claim 1 wherein the magnitude threshold is proportional to the long-term representation.

22. The method of claim 21 wherein the magnitude threshold is a user-selectable multiple of the long-term representation.

23. The method of claim 21 wherein the magnitude threshold equals the long-term representation multiplied by a seizure threshold factor, the seizure threshold factor ranging from about 2 to 64.

24. The method of claim 23 wherein the seizure threshold factor is about 22.

25. A non-transitory computer-readable medium programmed with instructions for performing a method of detecting a neurological event, the medium comprising instructions for causing a programmable processor to:
sample an EEG signal at a sample rate to form a stream of sampled data values;
transform the stream of sampled data values into a stream of data magnitude values;
determine, with the programmable processor, a long-term representation of the EEG signal from the data magnitude values, comprising comparing a data magnitude value to a previous value of the long-term representation, and incrementing the previous value by a predetermined increment amount if the data magnitude value equals or exceeds the previous value, and decrementing the previous value by a predetermined decrement amount if the data magnitude value is less than the previous value;
derive a magnitude threshold from the long-term representation;
compare the data magnitude values to the magnitude threshold to produce a stream of comparator output values, each comparator output value indicating whether a given data magnitude value exceeds the magnitude threshold;
calculate an event monitoring parameter based on a rolling window of comparator output values;
compare the event monitoring parameter to an onset threshold; and
detect a neurological event when the event monitoring parameter exceeds the onset threshold.

26. A method of detecting a neurological event, the method comprising:
acquiring an EEG signal comprising a stream of sampled data values;
transforming the stream of sampled data values into a stream of data magnitude values;
determining a long-term representation of the EEG signal from the data magnitude values;
deriving a magnitude threshold from the long-term representation;
comparing the data magnitude values to the magnitude threshold to produce a stream of comparator output values, each comparator output value consisting of a binary value indicating whether a given data magnitude value exceeds the magnitude threshold;
calculating an event monitoring parameter with processing circuitry, consisting of summing the comparator output values within a rolling window;
comparing the event monitoring parameter to an onset threshold; and
detecting a neurological event when the event monitoring parameter exceeds the onset threshold.

27. The method of claim 26 wherein the long-term representation is a long-term average of the data magnitude values.

28. The method of claim 26 wherein a neurological event is detected when the event monitoring parameter exceeds the onset threshold for an onset duration.

29. The method of claim 26 further comprising determining an end of a neurological event when the event monitoring parameter decreases below a termination threshold.

30. The method of claim 29 further comprising assigning a predetermined initial value to the long-term representation at the end of a neurological event.

31. The method of claim 26 wherein the magnitude threshold is a user-selectable multiple of the long-term representation.

32. A method of detecting a neurological event, the method comprising:
acquiring an EEG signal comprising a stream of sampled data values;
transforming the stream of sampled data values into a stream of data magnitude values;
determining, with processing circuitry, a long-term representation of the EEG signal from the data magnitude values, wherein determining the long-term representation comprises comparing a data magnitude value to a previous value of the long-term representation, and incrementing the previous value by a predetermined increment amount if the data magnitude value equals or exceeds the previous value, and decrementing the previous value by a predetermined decrement amount if the data magnitude value is less than the previous value;

deriving a magnitude threshold from the long-term representation;

comparing the data magnitude values to the magnitude threshold to produce a stream of comparator output values, each comparator output value indicating whether a given data magnitude value exceeds the magnitude threshold;

calculating an event monitoring parameter based on a sum of comparator output values within a rolling window;

comparing the event monitoring parameter to an onset threshold; and detecting a neurological event when the event monitoring parameter exceeds the onset threshold.

* * * * *